(12) United States Patent
Rajagopalan et al.

(10) Patent No.: US 9,875,560 B2
(45) Date of Patent: Jan. 23, 2018

(54) GRAPHICAL DISPLAY OF PHYSIOLOGICAL PARAMETERS ON PATIENT MONITORS

(71) Applicant: Mindray DS USA, Inc., Mahwah, NJ (US)

(72) Inventors: Cadathur Rajagopalan, Dumont, NJ (US); Scott Eaton, Briarcliff Manor, NY (US); Elizabeth Rosenberg, Dobbs Ferry, NY (US); Christine Galanido, Hackensack, NJ (US)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 376 days.

(21) Appl. No.: 14/543,651

(22) Filed: Nov. 17, 2014

(65) Prior Publication Data

US 2015/0138205 A1   May 21, 2015

Related U.S. Application Data

(60) Provisional application No. 61/905,029, filed on Nov. 15, 2013, provisional application No. 61/970,740, filed on Mar. 26, 2014.

(51) Int. Cl.
| | |
|---|---|
| *G06T 11/20* | (2006.01) |
| *G06F 19/00* | (2011.01) |
| *A61B 5/021* | (2006.01) |
| *A61B 5/024* | (2006.01) |
| *A61B 5/00* | (2006.01) |

(52) U.S. Cl.
CPC ............ *G06T 11/203* (2013.01); *A61B 5/742* (2013.01); *G06F 19/3487* (2013.01); *G06T 11/206* (2013.01); *A61B 5/021* (2013.01); *A61B 5/024* (2013.01); *A61B 5/746* (2013.01); *G06F 19/3406* (2013.01); *G06T 2210/41* (2013.01)

(58) Field of Classification Search
None
See application file for complete search history.

(56) References Cited

U.S. PATENT DOCUMENTS

| | | | | |
|---|---|---|---|---|
| 2009/0054743 | A1* | 2/2009 | Stewart | G06T 11/206 600/301 |
| 2011/0201911 | A1* | 8/2011 | Johnson | A61B 5/14532 600/365 |
| 2011/0282705 | A1* | 11/2011 | Vucina | G06Q 10/06 705/7.13 |
| 2017/0000426 | A1* | 1/2017 | Harper | A61B 5/14532 |

* cited by examiner

*Primary Examiner* — James A Thompson
(74) *Attorney, Agent, or Firm* — Kory D. Christensen; Polsinelli LLP

(57) ABSTRACT

A system for receiving one or more measured physiological parameters of a patient and displaying a graphical representation of the same. In various embodiments, a display module generates a graphical display that includes a range of possible values for the physiological parameter, one or more thresholds and/or alarm values, a numeric display of the current value of the measured physiological parameter, and a historical comparator of the current value with historical values.

17 Claims, 24 Drawing Sheets

GRAPHICAL DISPLAY OF PHYSIOLOGICAL PARAMETERS ON PATIENT MONITORS

RELATED APPLICATIONS

This application claims priority to U.S. Provisional Patent Application No. 61/905,029, titled "Graphical Display of Physiological Parameters on Patient Monitors," filed on Nov. 15, 2013 and U.S. Provisional Patent Application No. 61/970,740, titled "Graphical Display of Physiological Parameters on Patient Monitors," filed on Mar. 26, 2014, which applications are both incorporated by reference in their entireties.

TECHNICAL FIELD

This disclosure relates to systems and techniques that help a clinician or other user quickly comprehend current, recent, and/or historical physiological parameters via a graphical representation.

SUMMARY

This disclosure generally relates to techniques to help a clinician or other user quickly comprehend current, recent, and/or historical physiological parameters via a graphical representation. In various embodiments, one or more physiological parameters are determined or received by a system configured to process and present related information to a user, such as a clinician or other healthcare worker or interested party. The physiological parameters are displayed via an electronic display and may allow the user to compare the current value of one or more physiological parameters with other useful information.

For example, the electronic display may allow for a quick comparison of a current physiological parameter with threshold (high and/or low) values, historical values, values from a previous time period, normal values, normalized values, general averages, patient-specific averages, multiple stages of alarm levels, target values, danger zones, custom alarms, and the like.

In some embodiments, historical data may be presented as a ghost image, a line, a graph, and/or other feature as described herein. Alarms limits, thresholds, and maximum and minimum values may be shown as numerical values and/or by representation through the use of one or more icons or symbols. Similarly, the current value of a physiological parameter may be shown as a numeric value and/or through representation by a graphic, an icon, and/or a symbol.

In various embodiments, the electronic display may be configured to display a semicircle, a semi-ellipse, a partial circle, a partial ellipse, a rectangle, a square, a triangle, or any other geometric shape or n-side polygon. In various embodiments, the display may be a custom shape that has any number of curves and/or sides.

DETAILED DESCRIPTION

Figure 1:
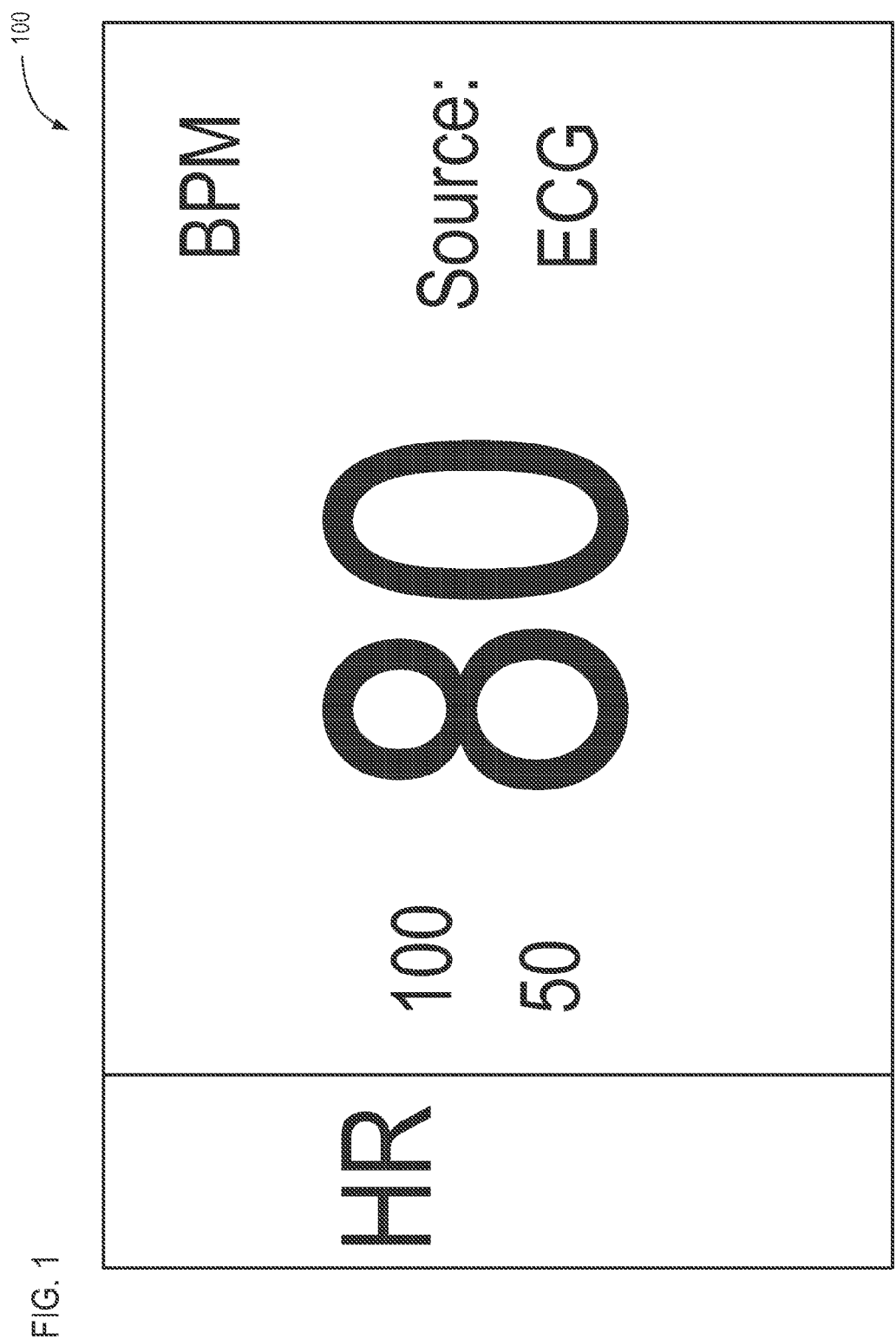
FIG. 1 is a tiled display of a measured heart rate parameter that may be displayed on a physiological parameter monitoring equipment, according to one embodiment.

This disclosure generally relates to techniques to help a clinician or other user quickly comprehend current, recent, and/or historical physiological parameters via a graphical representation. In various embodiments, one or more physiological parameters are determined or received by a system configured to process and present related information to a user, such as a clinician or other healthcare worker or interested party. The physiological parameters may be received by the system via a network or other data connection. In other embodiments, the system may include one or more connections ports for probes and/or sensors for measuring patient physiological parameters.

The physiological parameters are displayed via an electronic display. The physiological parameters may be shown with a visual comparison with historical physiological parameters, custom alarms, predefined thresholds, and/or the like.

For example, the electronic display may allow for a quick comparison of a current physiological parameter with threshold (high and/or low) values, historical values, values from a previous time period, normal values, normalized values, general averages, patient-specific averages, multiple stages of alarm levels, target values, danger zones, custom alarms, and the like.

In some embodiments, historical data may be presented as a ghost image. The ghost image may be a single historical value or an average of historical values during a time period. The time period may be user selectable or may be predefined as a number of minutes, hours, days, weeks, or even years. Multiple historical values may be displayed using multiple ghost images of historical values (averages, relative, or absolute) from prior time periods.

Historical data may also be illustrated as a line, a graph, and/or other feature as described herein. Alarms limits, thresholds, and maximum and minimum values may be shown as numerical values and/or by representation through the use of one or more icons or symbols. Similarly, the current value of a physiological parameter may be shown as a numeric value and/or through representation by a graphic, an icon, and/or a symbol.

In various embodiments, the electronic display may be configured to display a semicircle, a semi-ellipse, a partial circle, a partial ellipse, a rectangle, a square, a triangle, or any other geometric shape or n-side polygon. In various embodiments, the display may be a custom shape that has any number of curves and/or sides.

A physiological parameter presentation system may be computerized and may include, incorporate, utilize, and/or otherwise rely on various processors, memory, software modules, hardware components, electronic connectors, ports, communication components, and the like. An electronic input receiver may receive electronic values corresponding to measured physiological parameters. In some embodiments, the system may receive the values of physiological parameters via a data or network connection. In other embodiments, the system may include probe and/or sensor ports for connection to probes and/or sensors for measuring physiological parameters.

The physiological parameter presentation system may include a data store to store historical values. The data store may be remote and accessible via a network connection and/or locally accessible. The system may generate a graphical display via a display module. The display module may be implemented as a software program, hardware circuitry, and/or a combination thereof.

The display module may generate a graphical display of the physiological parameter(s) that includes one or more of a range of possible values for the physiological parameter, a visual representation of one or more threshold values, a numerical display of the current value of the measured physiological parameter, and a historical comparator based on one or more of the historical values of the measured physiological parameter. The generated graphical display may then be output to an electronic display for visualization by a clinician or other user.

In various embodiments, the historical comparator is a ghost image of a historical value of the physiological parameter. In some embodiments, the historical comparator is a ghost image of an average of historical values of the physiological parameter during a prior time period. The time period may be user-selected, adjusted, and/or a predefined preset.

In some embodiments, the historical comparator is an extent indicator (e.g., an arrow, a line, a bar, etc.) that indicates a minimum historical value and a maximum historical value of the physiological parameter during a prior time period. In other embodiments, the historical comparator is a historical line showing past values. For example, the historical line may be a line that extends from a current value of the physiological parameter on an outer perimeter of a semicircle to a base of the semicircle, such that the most recent historical values are positioned closest to the outer perimeter of the semicircle and the oldest historical values are positioned closest to the base of the semicircle.

As previously described, the graphical display may show minimum and maximum possible values of the physiological parameters in rectangular, circular, semicircular, and/or other gauge shapes. An extend indicator, a ghost image, and/or a historical line may be shown on rectangular, circular, semicircular, and/or other gauge shapes.

The embodiments of the disclosure are described below with reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor do the steps or sequences of steps need to be executed only once or even in the same order in subsequent repetitions.

Embodiments may include various steps, which may be embodied in machine-executable instructions to be executed by a computer system. A computer system includes one or more general-purpose or special-purpose computers (or other electronic devices). The computer system may include hardware components that include specific logic for performing the steps or may include a combination of hardware, software, and/or firmware.

Embodiments may also be provided as a computer program product including a computer-readable medium having stored thereon instructions that may be used to program a computer system or other electronic device to perform the processes described herein. The computer-readable medium may include, but is not limited to: hard drives, floppy diskettes, optical disks, CD-ROMs, DVD-ROMs, ROMs, RAMs, EPROMs, EEPROMs, magnetic or optical cards, solid-state memory devices, or other types of media/computer-readable media suitable for storing electronic instructions.

Computer systems and the computers in a computer system may be connected via a network. Suitable networks for configuration and/or use as described herein include one or more local area networks, wide area networks, metropolitan area networks, and/or Internet or IP networks, such as the World Wide Web, a private Internet, a secure Internet, a value-added network, a virtual private network, an extranet, an intranet, or even stand-alone machines which communicate with other machines by physical transport of media. In particular, a suitable network may be formed from parts or entireties of two or more other networks, including networks using disparate hardware and network communication technologies.

One suitable network includes a server and several clients; other suitable networks may contain other combinations of servers, clients, and/or peer-to-peer nodes, and a given computer system may function both as a client and as a server. Each network includes at least two computers or computer systems, such as the server and/or clients. A computer system may include a workstation, laptop computer, disconnectable mobile computer, server, mainframe, cluster, so-called "network computer" or "thin client," tablet, smart phone, personal digital assistant or other hand-held computing device, "smart" consumer electronics device or appliance, medical device, or a combination thereof.

Suitable networks may include communications or networking software, such as the software available from Novell, Microsoft, Artisoft, and other vendors, and may operate using TCP/IP, SPX, IPX, and other protocols over twisted pair, coaxial, or optical fiber cables, telephone lines, radio waves, satellites, microwave relays, modulated AC power lines, physical media transfer, and/or other data transmission "wires" known to those of skill in the art. The network may encompass smaller networks and/or be connectable to other networks through a gateway or similar mechanism.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

As used herein, a software module or component may include any type of computer instruction or computer-executable code located within a memory device. A software module may, for instance, include one or more physical or logical blocks of computer instructions, which may be organized as a routine, program, object, component, data structure, class, etc., that perform one or more tasks or implement particular abstract data types. It is appreciated that a software module may be implemented in hardware and/or firmware instead of or in addition to software. One or more of the functional modules described herein may be separated into sub-modules and/or combined into a single or smaller number of modules.

In certain embodiments, a particular software module may include disparate instructions stored in different locations of a memory device, different memory devices, or different computers, which together implement the described functionality of the module. Indeed, a module may include a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Much of the infrastructure that can be used according to the present invention is already available, such as general purpose computers, computer programming tools and techniques, computer networks and networking technologies, digital storage media, authentication, access control, and other security tools and techniques provided by public keys, encryption, firewalls, and/or other means.

Figure 2:
FIG. 2 is a tiled display of a measured blood pressure parameter that may be displayed on a physiological parameter monitoring equipment, according to one embodiment.

FIG. 1 is a tiled display 100 of a measured heart rate parameter that may be displayed on a physiological parameter monitoring equipment, according to one embodiment. The tiled display 100 may show the current value of the physiological parameter, and may include an alarm limit, threshold values, and/or other information. FIG. 2 is a similar tiled display 200 of a measured blood pressure parameter that may be displayed on a physiological parameter monitoring equipment. The physiological parameters of FIGS. 1 and 2 may be displayed on the same display simultaneously or may require toggling between views. To see historical data, alarms, selected threshold values, and other information, the clinician may need to toggle between various screens or display modes.

The present systems and methods allow historical data, alarms, threshold values, and other information to be viewed on the same screen in a format that is quickly understood. The present systems and methods allow for historical variation in a physiological parameter to be viewed concurrently with the current value. Unlike conventional numerical tiles, the present systems and methods allow for multiple high and low alarm limits and/or threshold values to be shown, icons indicating whether or not the physiological parameter is within normal limits, short term trends, range of variation, and the like to be viewed quickly and easily without changing display modes or adjusting display settings.

Example physiological parameters are shown including heart rate, blood pressure, and respiration rates. However, any of a wide variety of physiological parameter information may be used in conjunction with the presently described systems and methods. In fact, other types of data and values may be displayed in a similar manner using the same principles discussed in conjunction with physiological parameter values.

Figure 3:
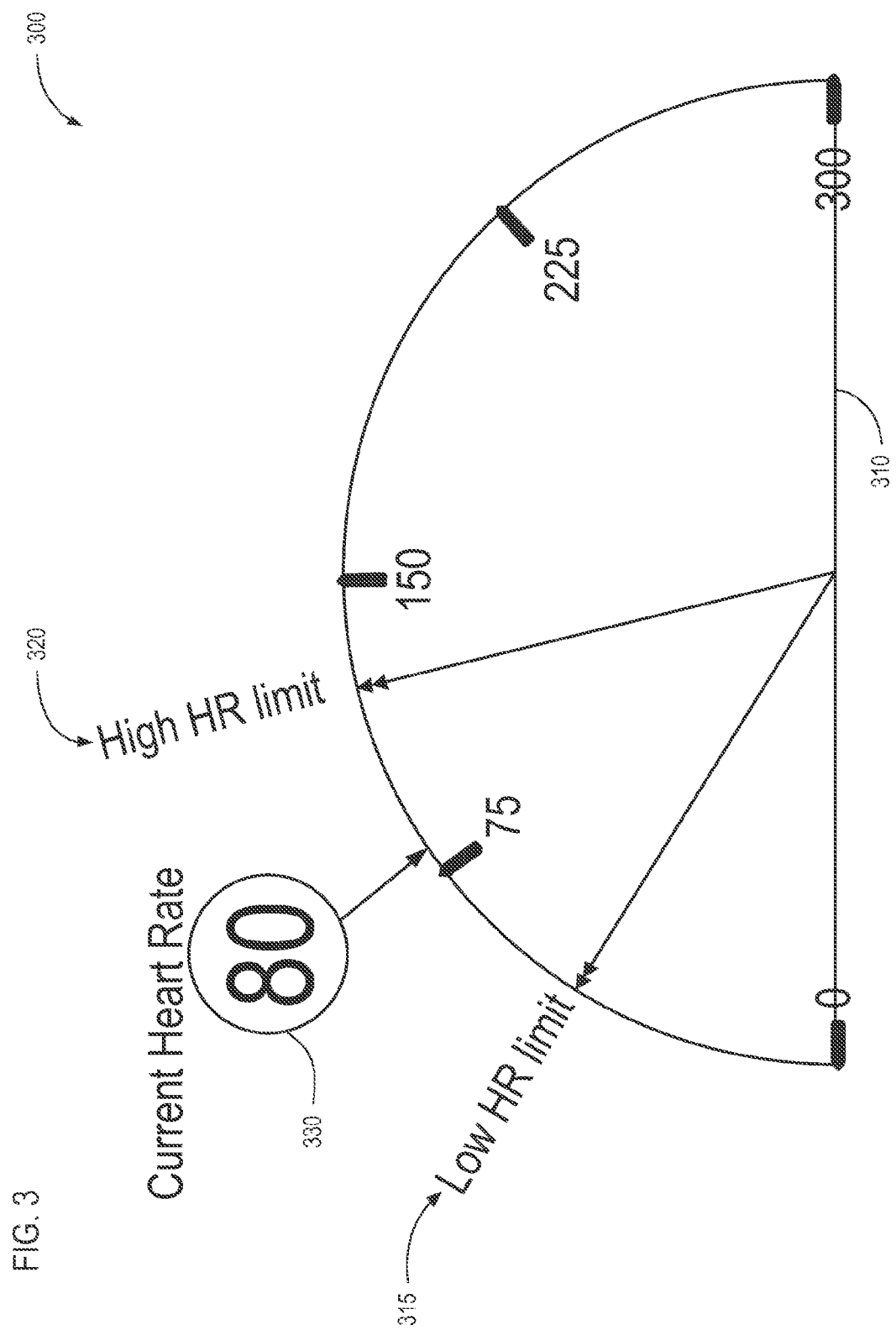
FIG. 3 is one embodiment of a graphical display of a physiological parameter in a semicircle presentation that includes a current value and threshold values.

FIG. 3 is one embodiment of a graphical display 300 of a physiological parameter in a semicircular gauge 310 presentation that includes a current value 330 and threshold values 315 and 320. As illustrated, the semicircular gauge 310 may graphically illustrate the current heart rate 330 relative to the low heart rate limit 315 and the high heart rate limit 320 all simultaneously.

Figure 4:
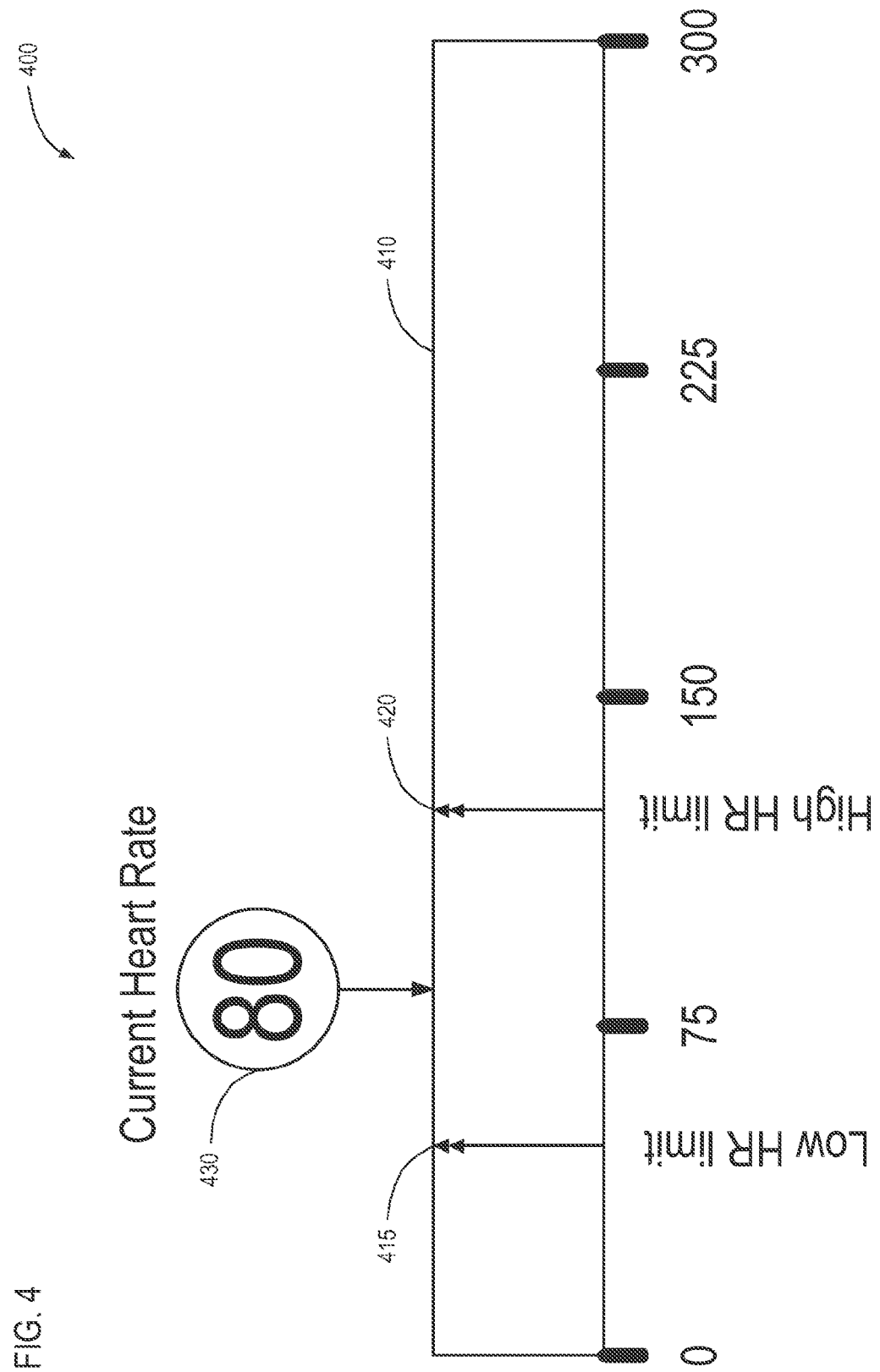
FIG. 4 is another embodiment of a graphical display of a physiological parameter in a rectangular presentation that includes a current value and threshold values.

FIG. 4 is another embodiment of a graphical display 400 of a physiological parameter in a rectangular presentation 410 that includes a current value 430 and threshold values 415 and 420. As illustrated, the current value 430 may be shown as a numerical value. The numerical value may be shown in a geometric shape, or may be colored, shaded, or otherwise highlighted.

Figure 5:
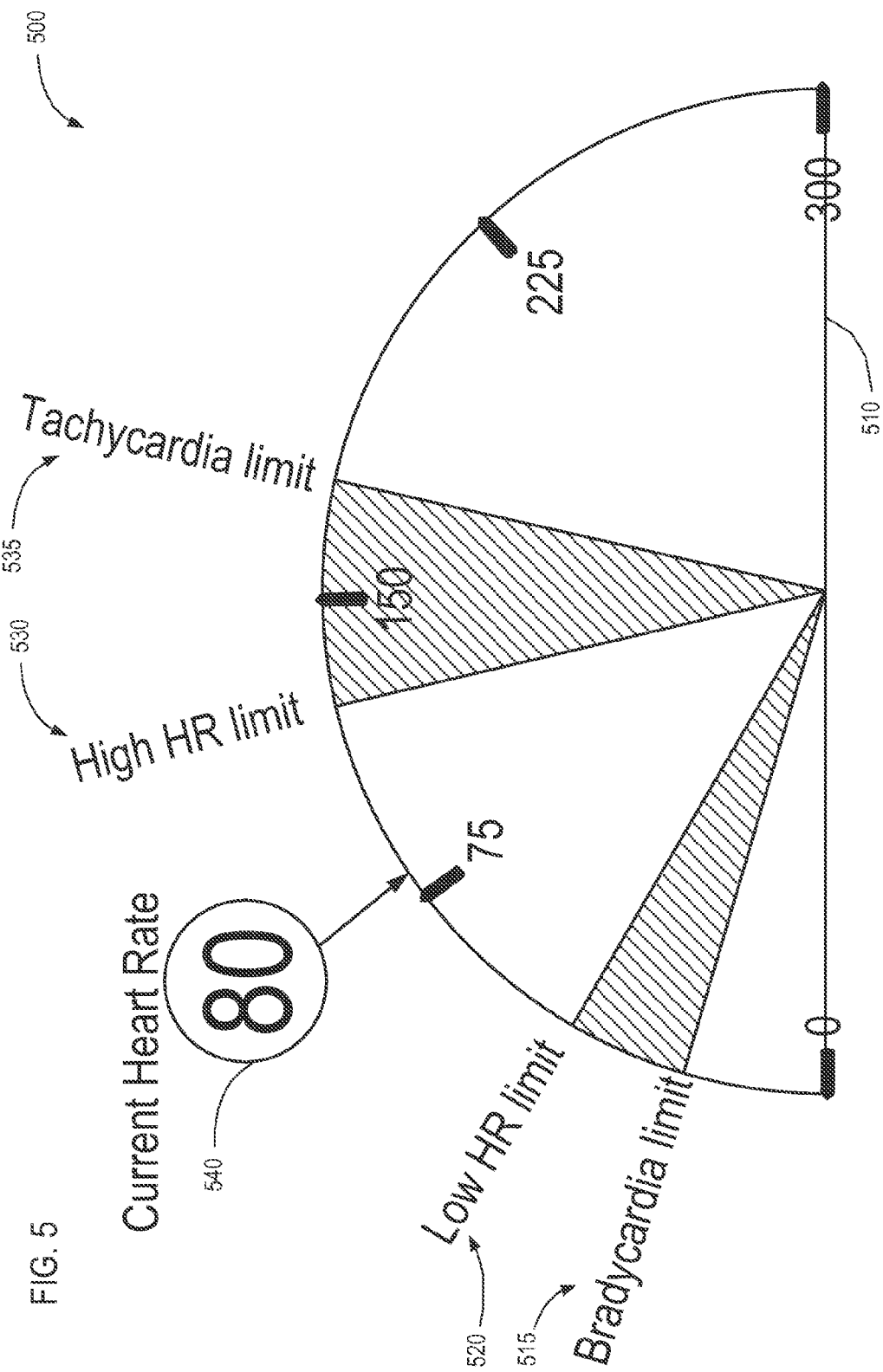
FIG. 5 is an embodiment of a graphical display of a physiological parameter in a semicircle that includes multiple threshold values and physiological parameter threshold zones.

FIG. 5 is an embodiment of a graphical display 500 of a physiological parameter in a semicircle 510 that includes multiple threshold values 515, 520, 530, and 535. The current value 540 of the physiological parameter may be shown along the outside perimeter of the semicircle. The threshold values may define threshold zones for the low values and the high values. Such zones may divide the semicircle into safe zones, warning zones, and danger zones. Alternative and/or additional intermediary zones may be added to the semicircle.

Figure 6:
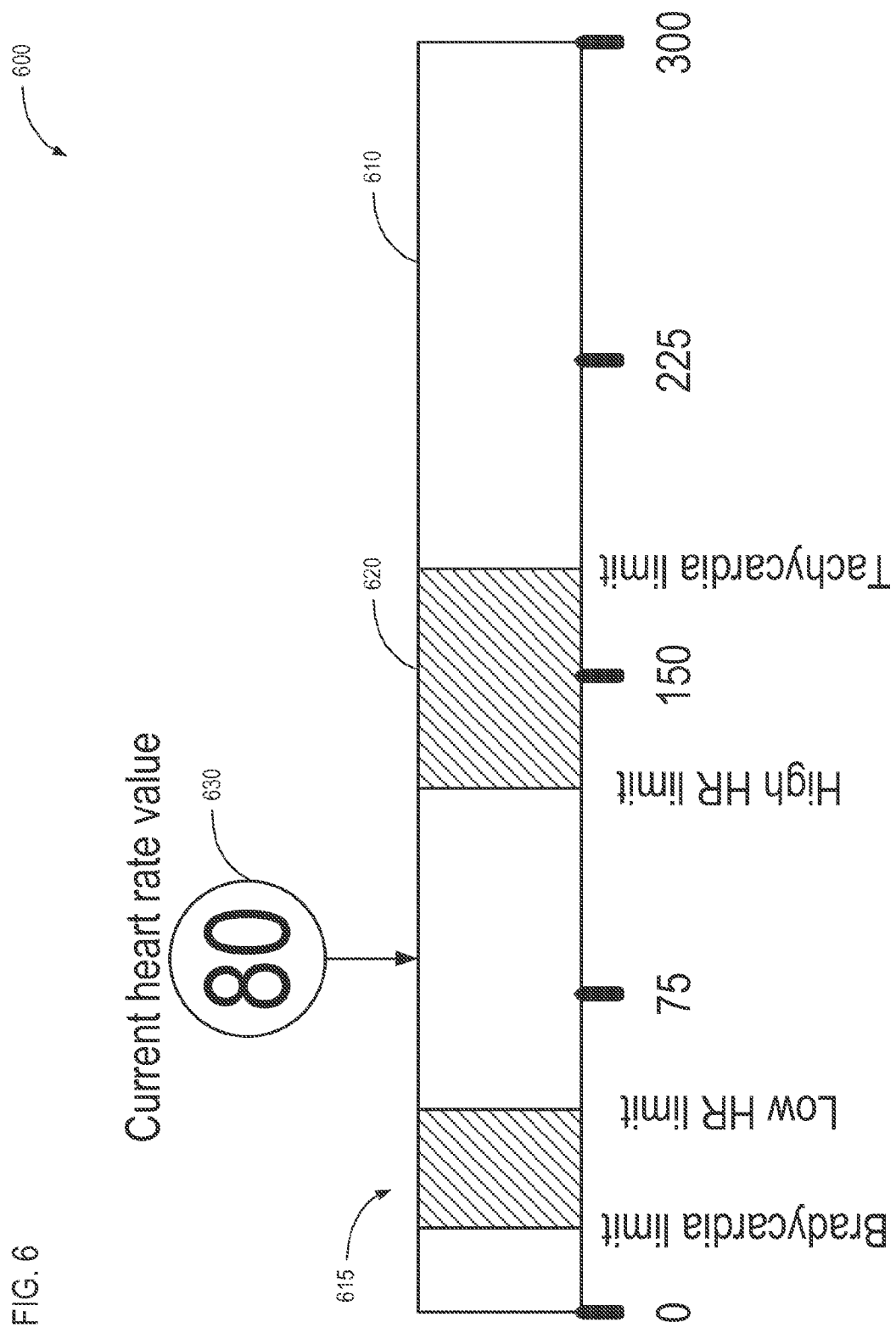
FIG. 6 is an embodiment of a graphical display similar to FIG. 5, in which a rectangle is used instead of a semicircle.

FIG. 6 is an embodiment of a graphical display 600 similar to FIG. 5, in which a rectangular gauge 610 is used instead of a semicircle gauge 510. Similar to FIG. 5, FIG. 6 illustrates a current value 630 of the physiological parameter, lower threshold zones 615 and upper threshold zones 620.

Figure 7:
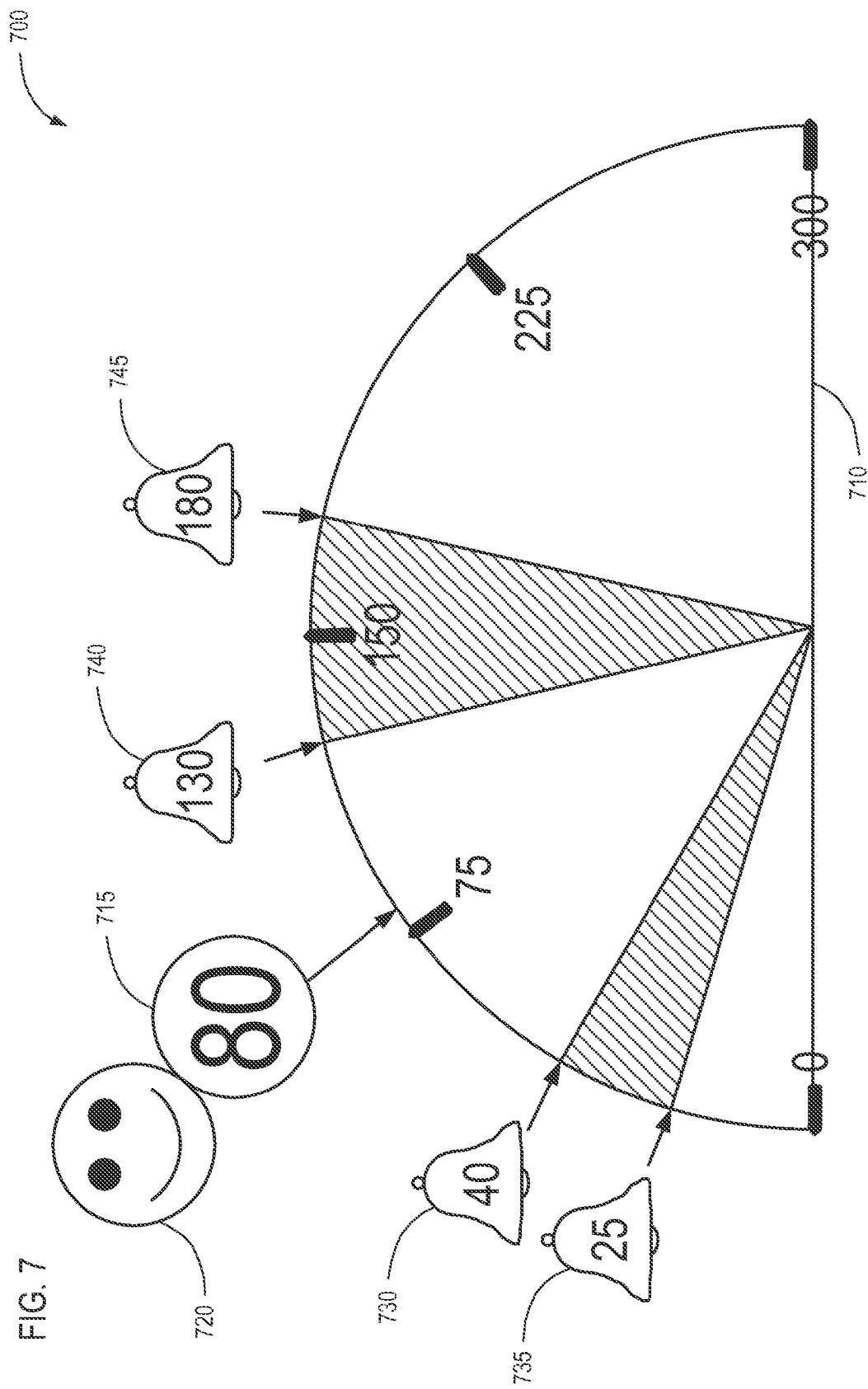
FIG. 7 is an embodiment of a graphical display of physiological parameters in a semicircle that includes multiple limits shown as alarm bells and an icon representing an acceptable status.

FIG. 7 is an embodiment of a graphical display 700 of a physiological parameter in a semicircle 710 that includes multiple limits shown as alarm bells 735, 730, 740, and 745. FIG. 7 also includes a graphical (numerical) display of the current value 715 of the physiological parameter. A status icon 720 (shown as a smiley face) may indicate whether or not the current value 715 of the physiological parameter is in an acceptable range. Different status icons may be used to indicate that the current value 715 is in a warning zone (e.g., a straight face) or danger zone (e.g., a frowny face). In some embodiments, different icons may be used to show that the current value is too low or too high.

Figure 8:
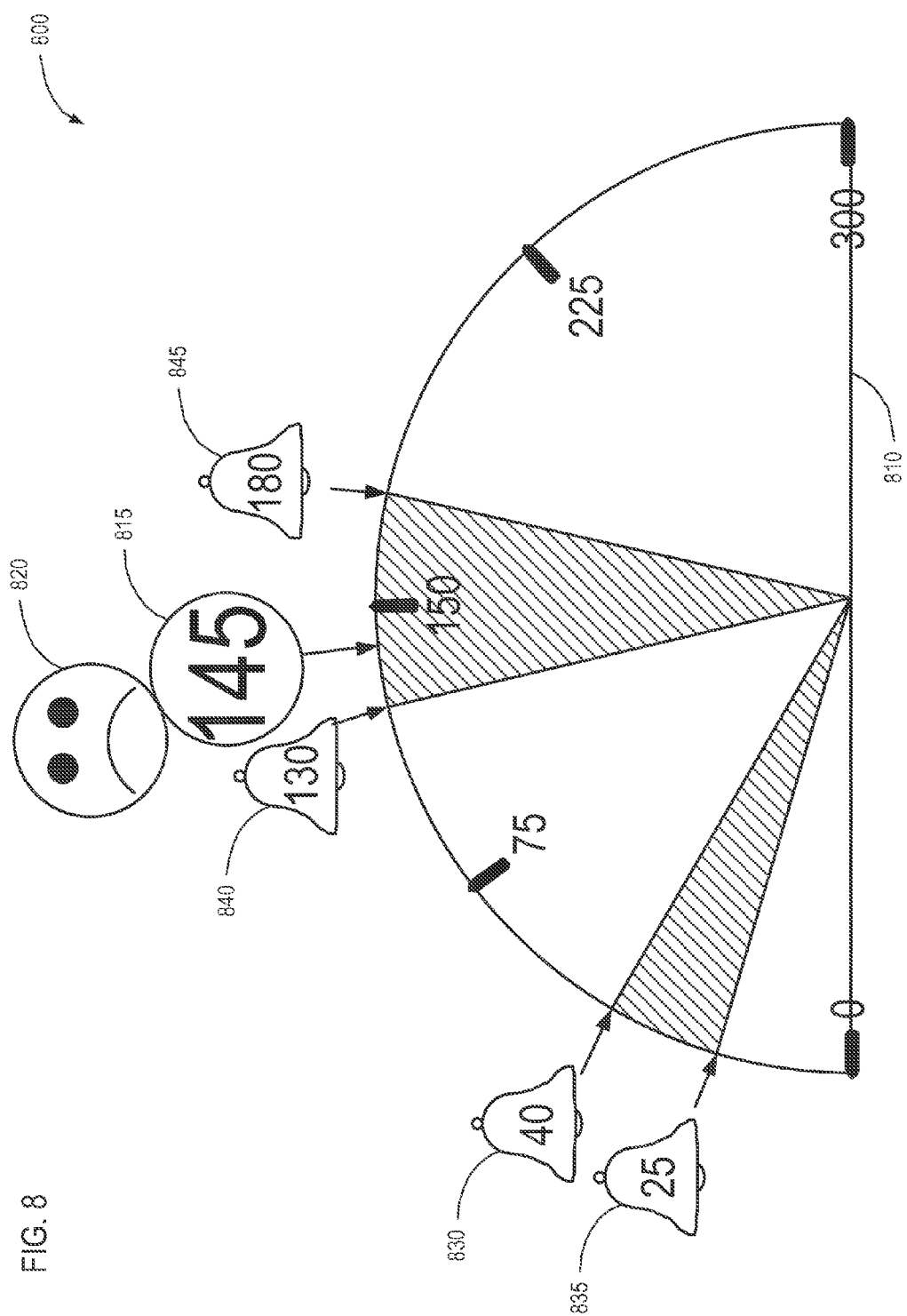
FIG. 8 illustrates the graphical display of FIG. 7 in which the physiological parameter is in an unacceptable zone and is represented by a corresponding icon.

FIG. 8 illustrates a graphical display 800 similar to that of FIG. 7 in which the physiological parameter is in an unacceptable zone (between alarm bells 840 and 845) along the semicircle 810. The status of the current value 815 is represented by a frowny status icon 820. If the current value 815 of the physiological parameter were within the lower zone defined between alarm bells 830 and 835, the same or a different status icon might be used.

Figure 9:
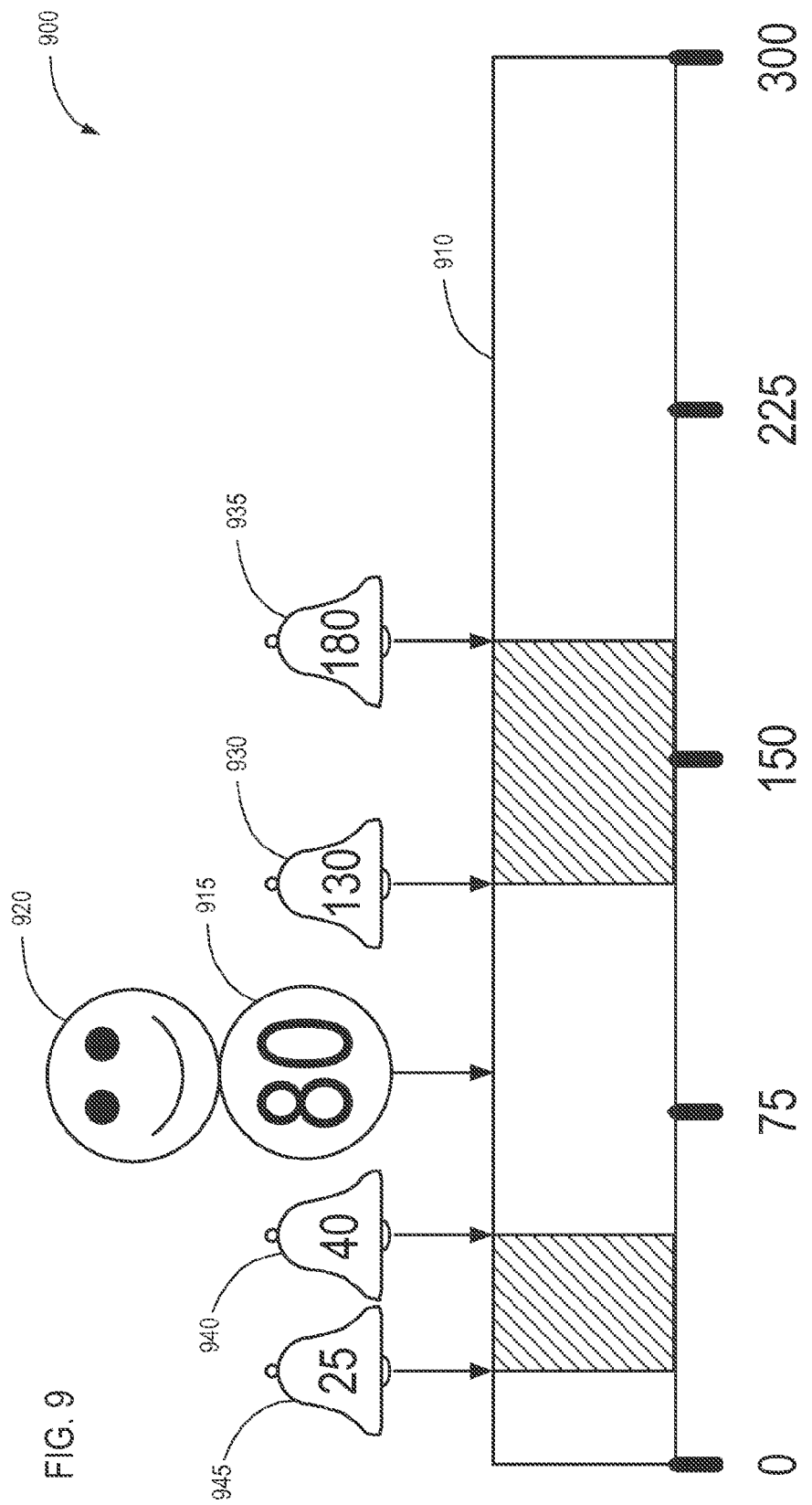
FIG. 9 illustrates a graphical display of a physiological parameter similar to FIG. 7 in a rectangular format.

FIG. 9 illustrates a graphical display 900 of a current value 915 along a rectangular gauge 910 showing the status of a physiological parameter relative to various alarm bells or threshold values 930, 935, 940, and 945. In the illustrated example, the status icon 920 is shown as a smiley face because the current value is within an acceptable zone.

Figure 10:
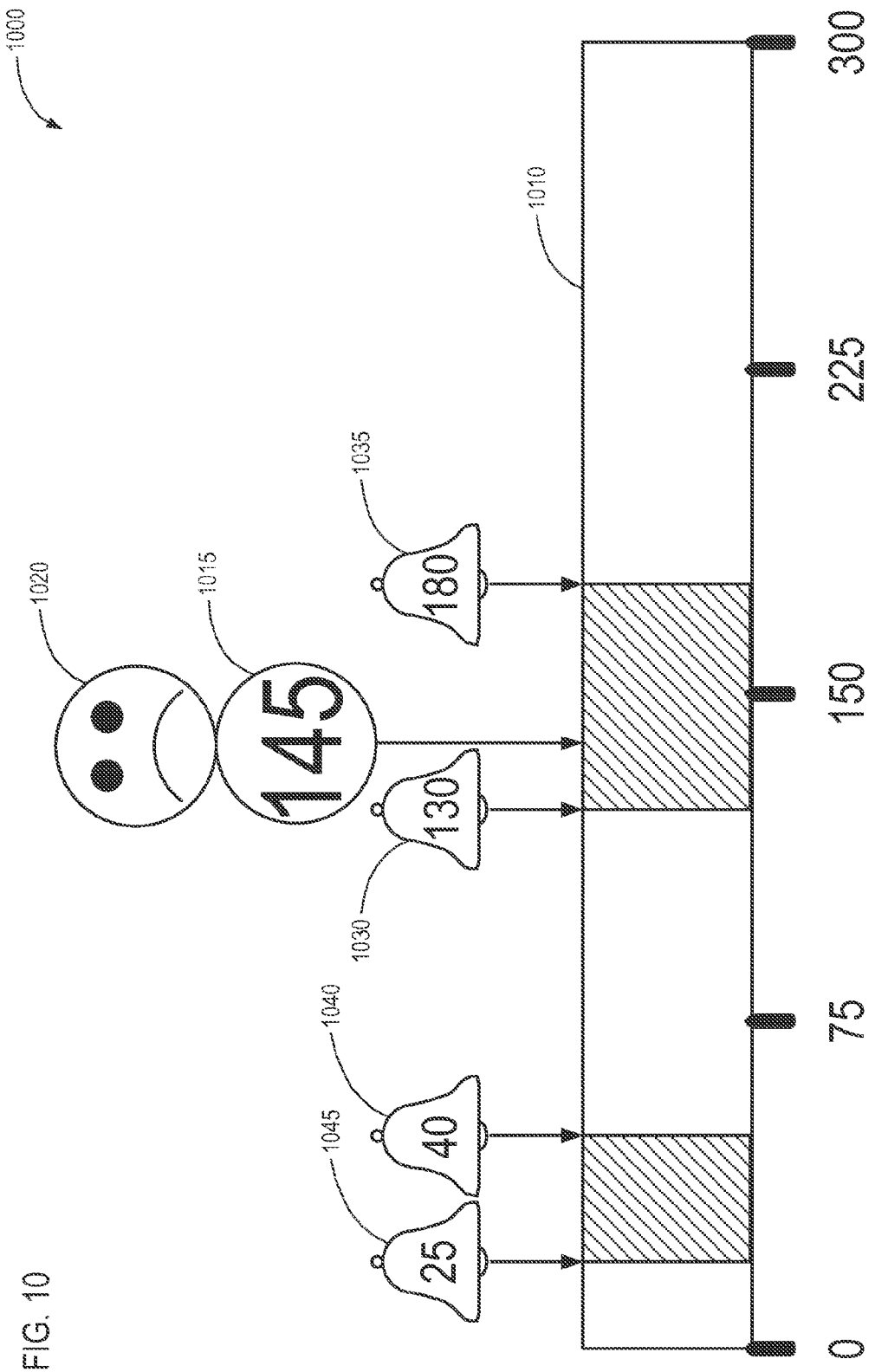
FIG. 10 illustrates a graphical display of a physiological parameter similar to FIG. 8 in a rectangular format.

FIG. 10 illustrates a graphical display 1000 of a current value 1015 along a rectangular gauge 1010 showing the status of a physiological parameter relative to various alarm bells or threshold values 1030, 1035, 1040, and 1045. In the illustrated example, the status icon 1020 is shown as a frowny face because the current value is outside of the acceptable zone.

Figure 11:
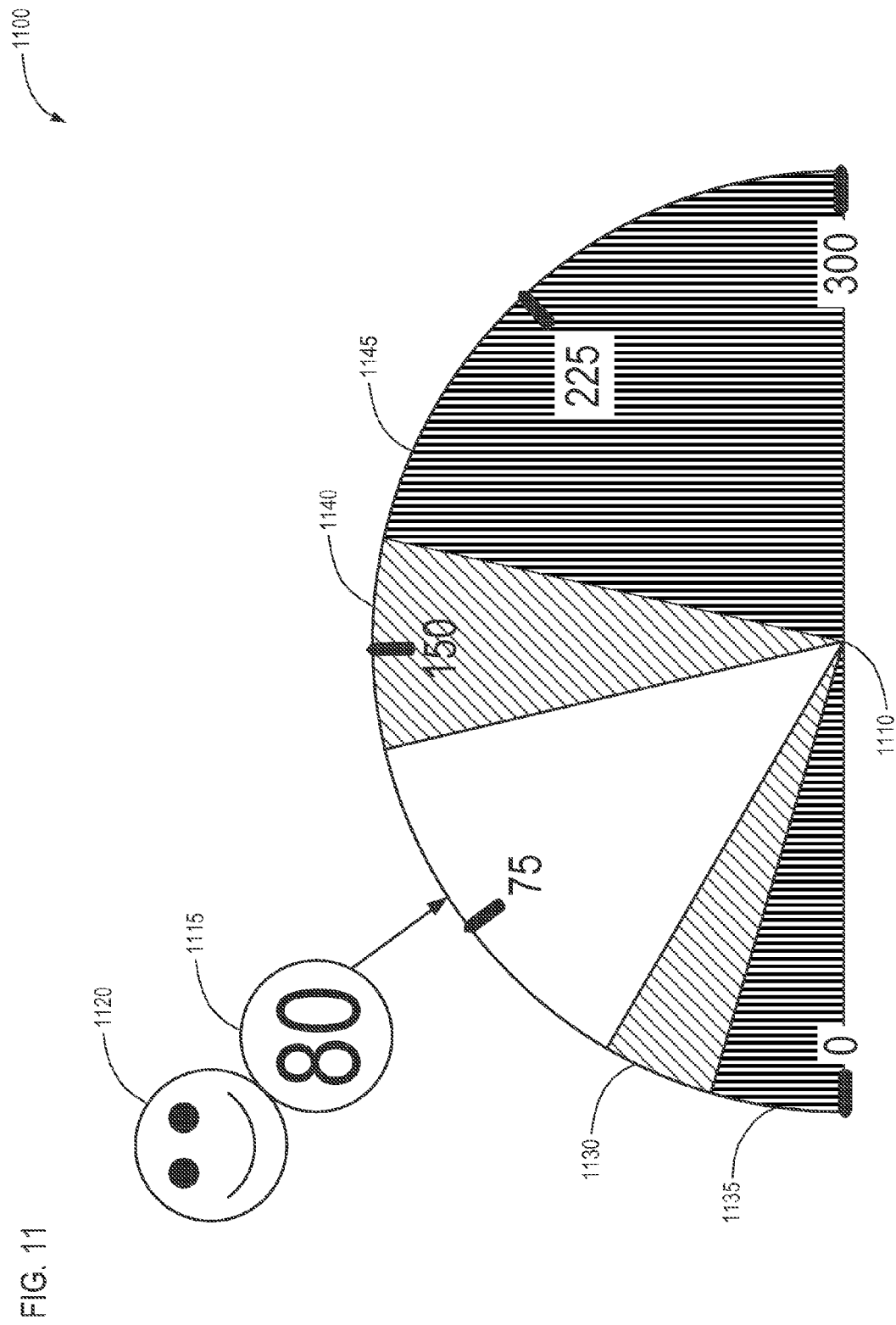
FIG. 11 illustrates a graphical display of a physiological parameter in which an icon represents an acceptable status and zones are color-coded (shaded) for acceptable, warning, and danger.

FIG. 11 illustrates a graphical display 1100 of a current value 1115 along a semicircular gauge 1110 showing the status of a physiological parameter relative to various threshold zones 1130, 1135, 1140, and 1145. In the illustrated example, the status icon 1120 is shown as a smiley face because the current value is within an acceptable zone.

Figure 12:
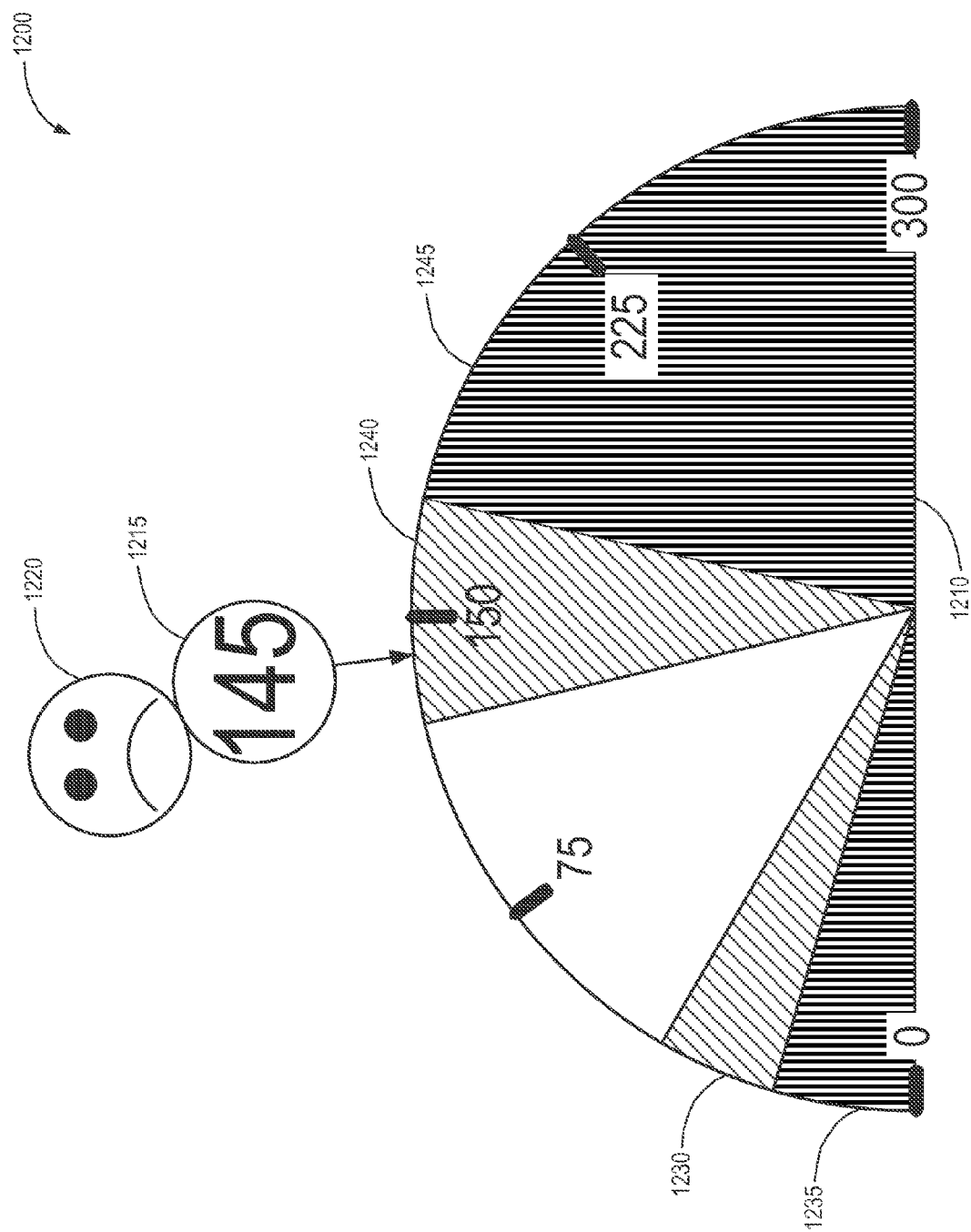
FIG. 12 illustrates a graphical display of a physiological parameter similar to that of FIG. 12 in which an icon represents that the current physiological parameter is in a warning zone.

FIG. 12 illustrates a graphical display 1200 of a current value 1215 along a semicircular gauge 1210 showing the status of a physiological parameter relative to various threshold zones 1230, 1235, 1240, and 1245. In the illustrated example, the status icon 1220 is shown as a frowny face because the current value is within a first stage of a danger zone, but not yet in a second, elevated stage of a danger zone.

Figure 13:
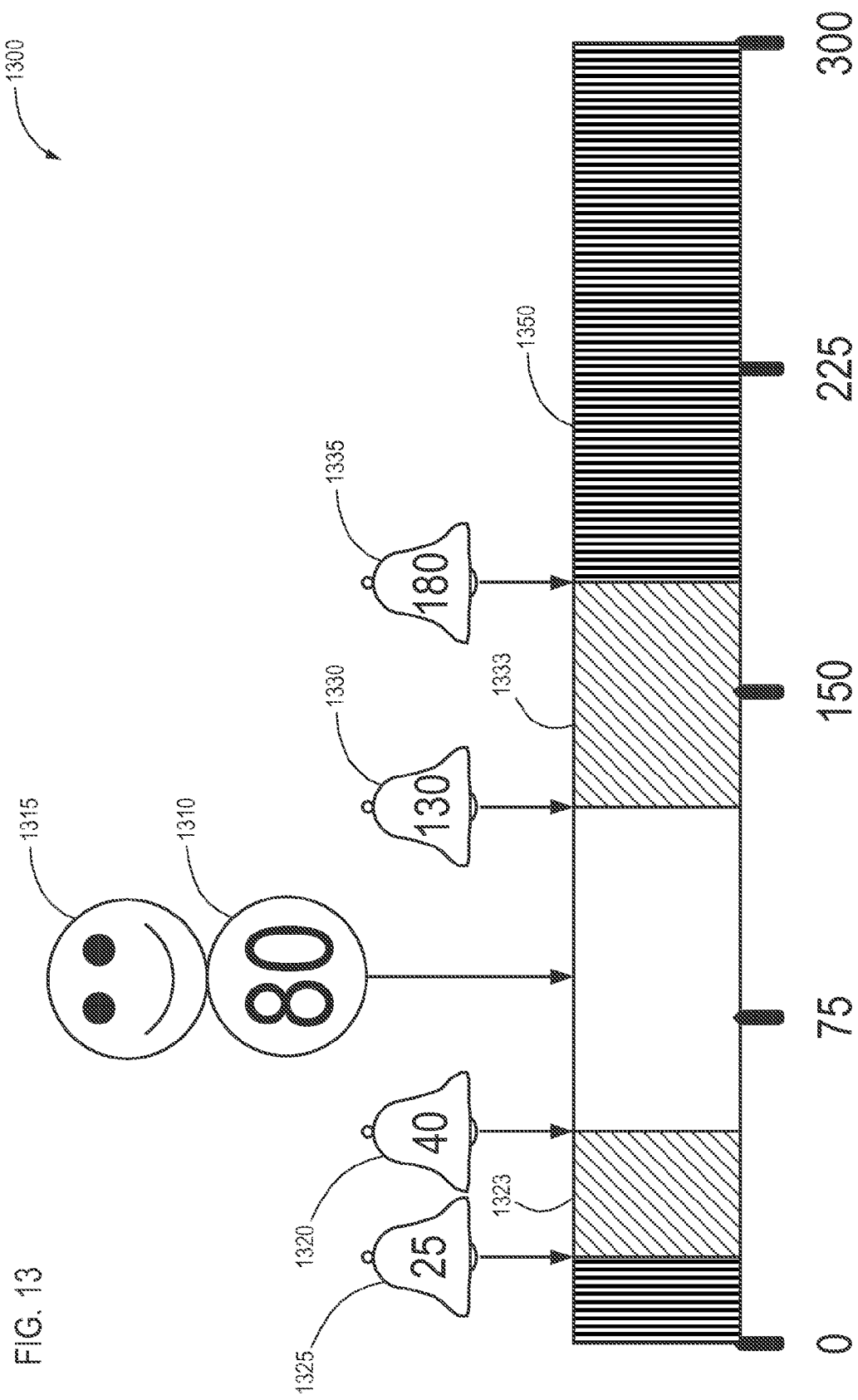
FIG. 13 illustrates a graphical display of a physiological parameter similar to that of FIG. 11 in a rectangular format.

FIG. 13 illustrates a graphical display 1300 of a current value 1310 along a rectangular gauge showing the status of a physiological parameter relative to various threshold zones 1323, 1333, and 1350. In the illustrated example, the status icon 1315 is shown as a smiley face because the current value is within an acceptable or a safe zone.

Figure 14:
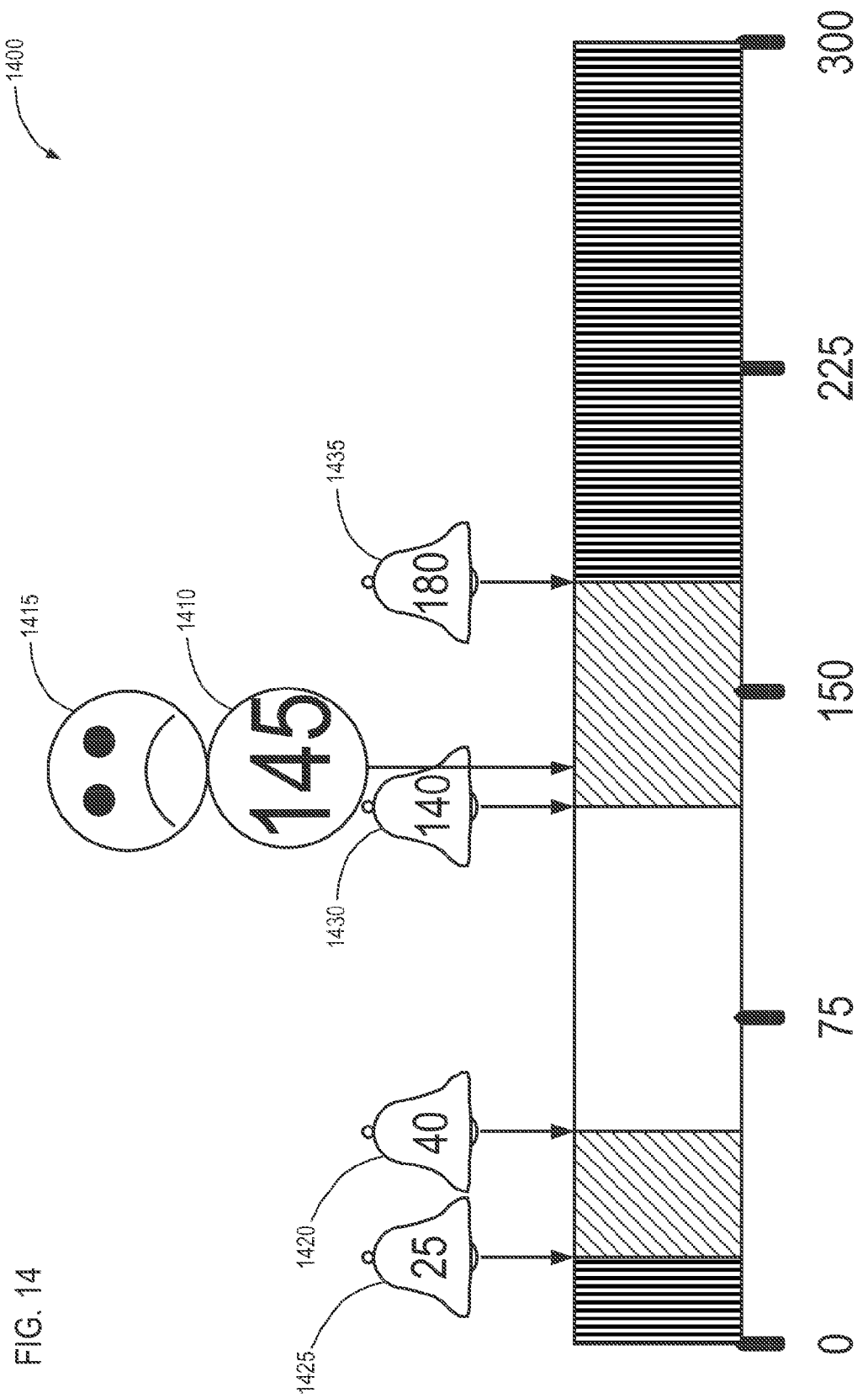
FIG. 14 illustrates a graphical display of a physiological parameter similar to that of FIG. 12 in a rectangular format.

FIG. 14 illustrates a graphical display 1400 of a current value 1410 along a rectangular gauge showing the status of a physiological parameter relative to various threshold zones. In the illustrated example, the status icon 1415 is shown as a frowny face because the current value is within a first stage of a danger zone defined by various alarm bells 1425, 1420, 1430, and 1435.

Figure 15:
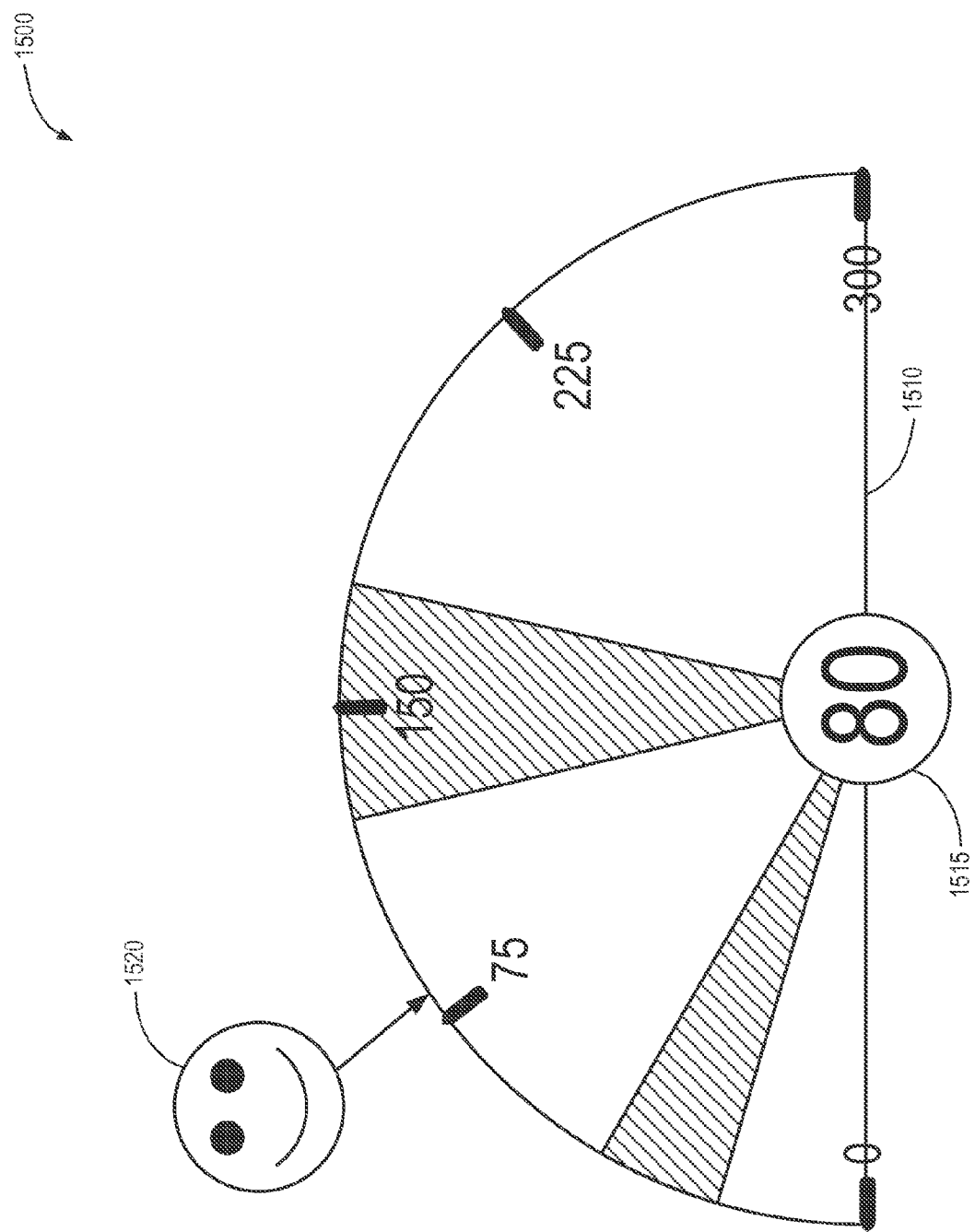
FIG. 15 illustrates a graphical display of a physiological parameter in which a current value is shown numerically in the center and graphically via a status icon around the perimeter of a semicircle.

FIG. 15 illustrates a graphical display 1500 of a physiological parameter in which a current value 1515 is shown numerically along the base of the semicircle 1510. A graphical status icon 1520 is shown along the perimeter of the semicircle 1510.

Figure 16:
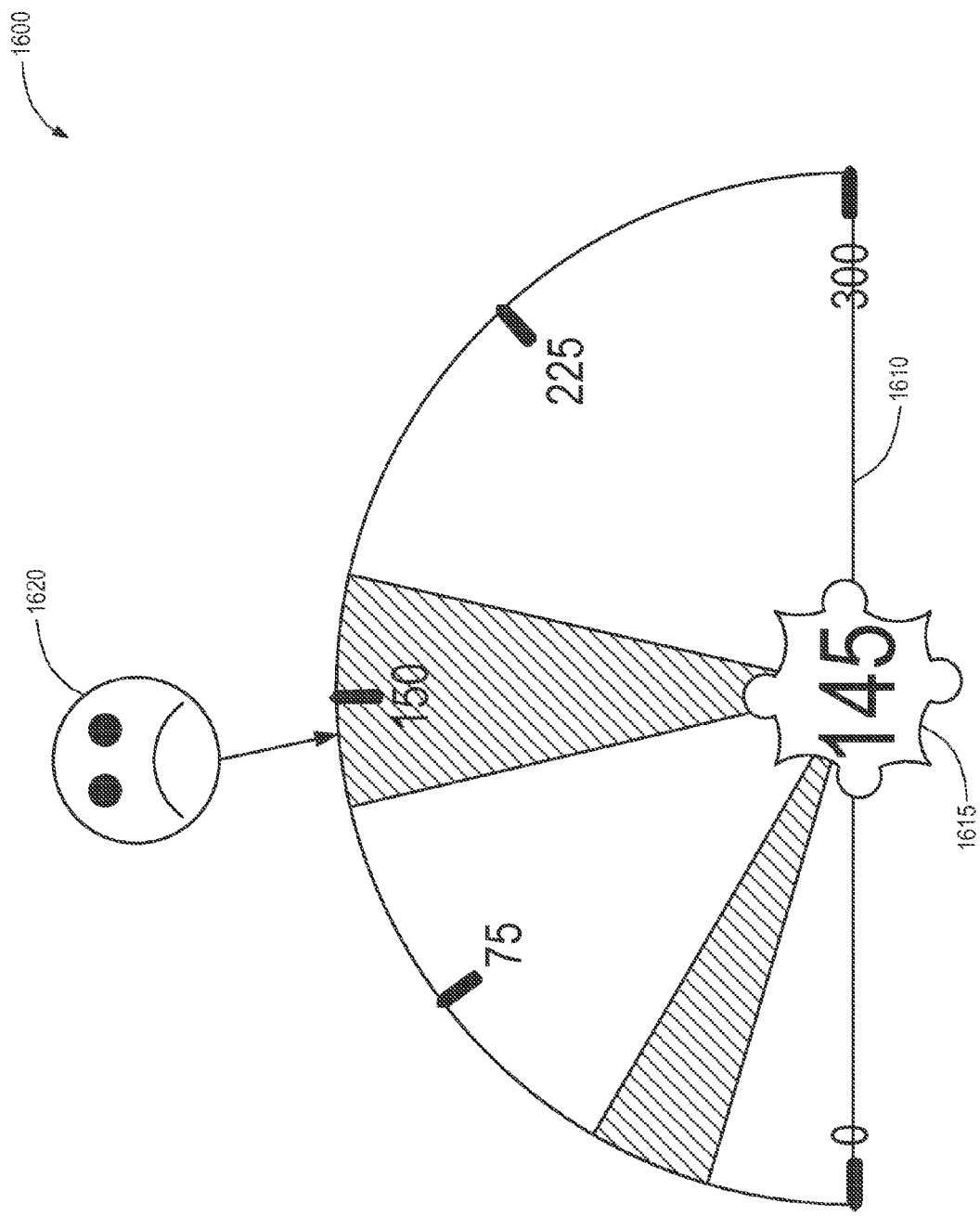
FIG. 16 is similar to FIG. 15 in which a current value of a physiological parameter is shown in the center and a status icon is shown around the perimeter of the semicircle.

FIG. 16 is similar to FIG. 15 in which a current value 1615 of a physiological parameter is shown in the center of the base of the semicircle 1610 and a status icon 1620 is shown around the perimeter of the semicircle 1610. The status icon 1620 is a frowny face to indicate that the current value 1615 is outside of an acceptable range.

Figure 17:
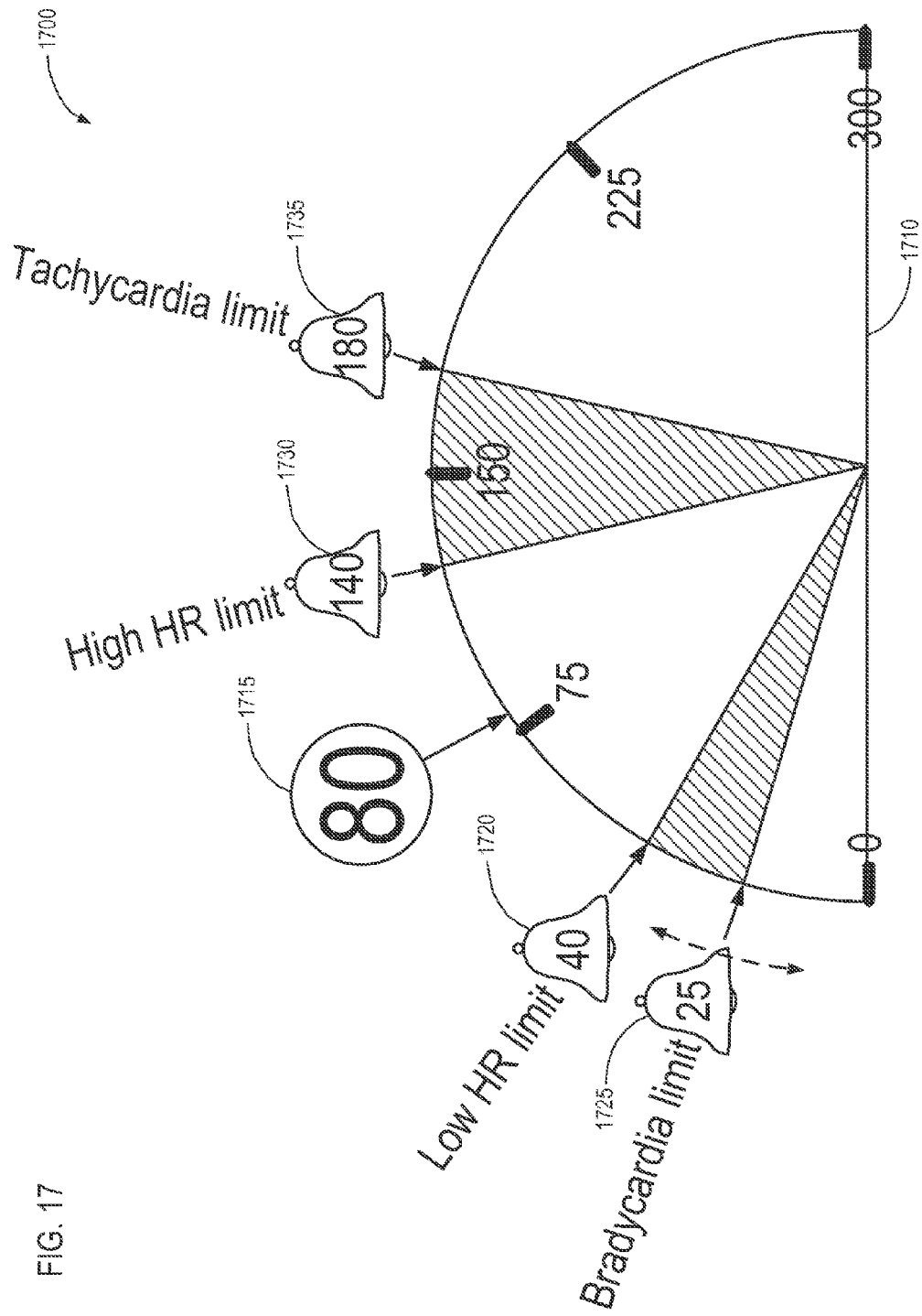
FIG. 17 illustrates a graphical display of a physiological parameter in which threshold values can be adjusted via a touchscreen interface.

FIG. 17 illustrates a graphical display 1700 of a physiological parameter in which threshold values 1720, 1725, 1730, and 1735 can be adjusted via a touchscreen interface. In various embodiments, custom alarms can be deleted, moved, renamed, changed, updated, and/or otherwise customized. A current value 1715 may be displayed as in other embodiments. The semicircle 1710 display can be modified by the user as well in various embodiments.

Figure 18:
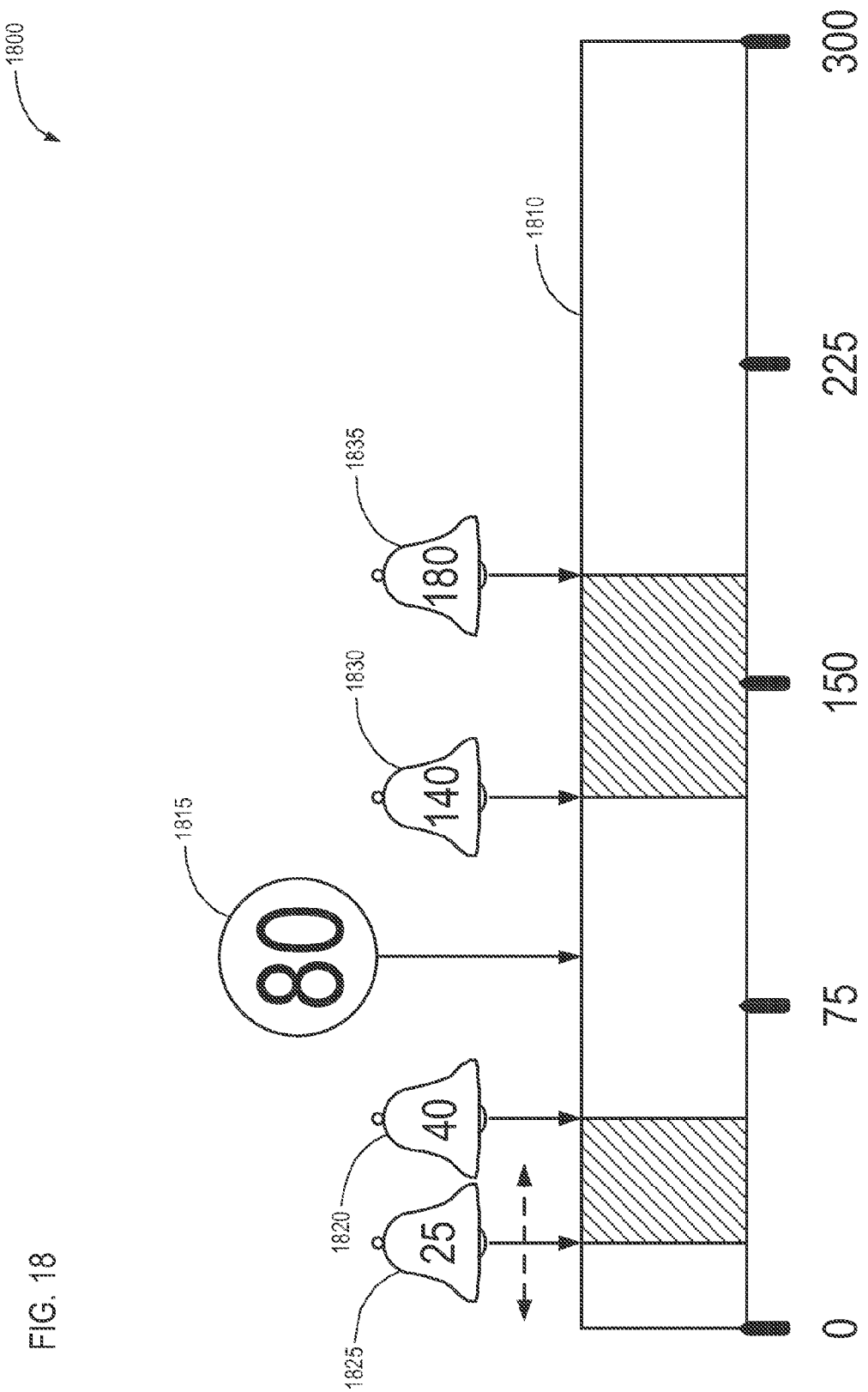
FIG. 18 illustrates a rectangular graphical display of a physiological parameter in which threshold values associated with a physiological parameter can be adjusted via a touchscreen interface.

FIG. 18 illustrates a graphical display 1800 of a physiological parameter in which threshold values 1820, 1825, 1830, and 1835 can be adjusted via a touchscreen interface. As illustrated, alarm (or threshold value) 1825 is being moved in any of the directions shown by the dashed arrows. In various embodiments, custom alarms can be deleted, moved, renamed, changed, updated, and/or otherwise customized. A current value 1815 may be displayed as in other embodiments. The rectangle 1810 display can be modified by the user as well in various embodiments. For example, it might be stretched, shortened, increased in height, and/or otherwise customized.

Figure 19:
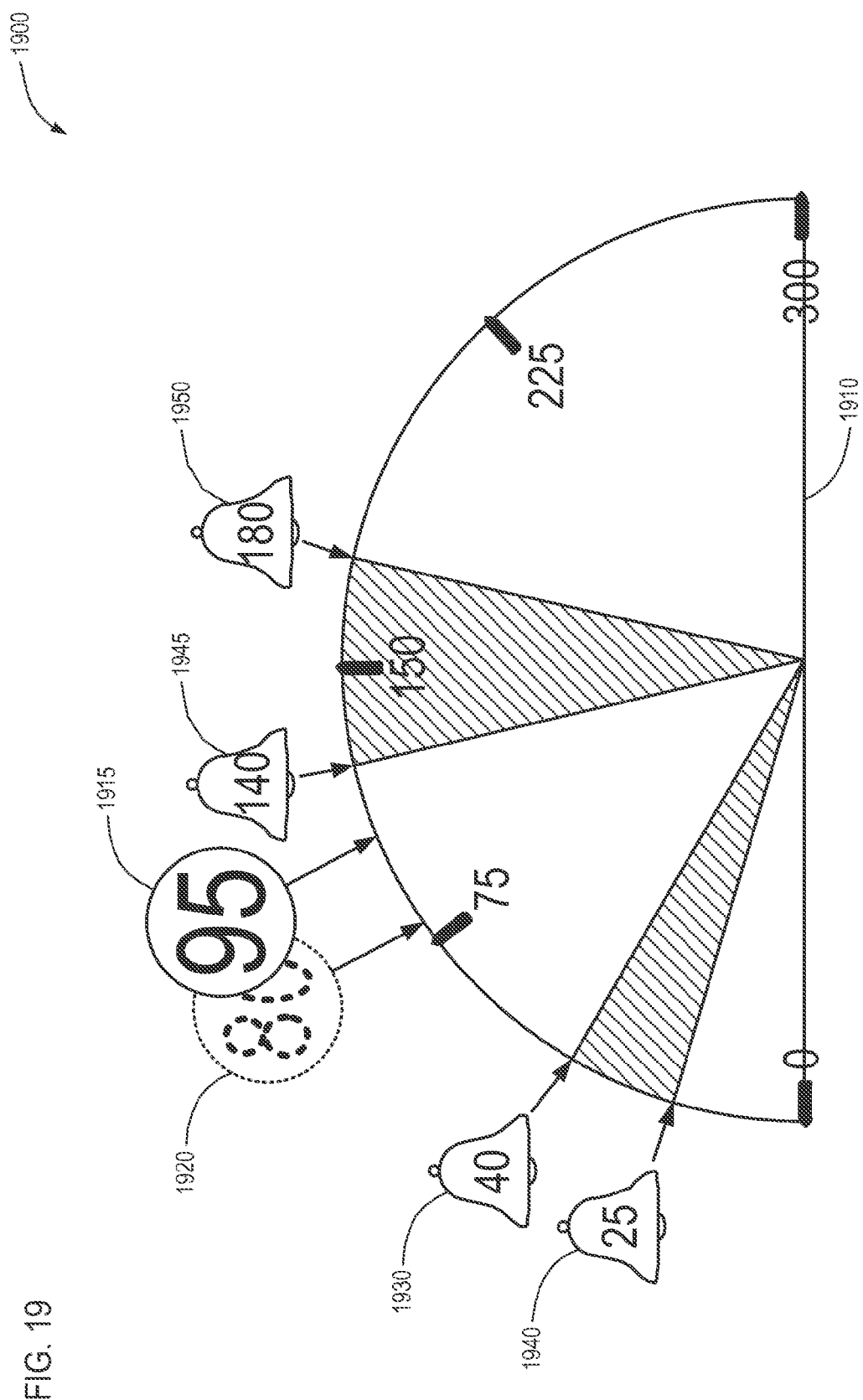
FIG. 19 illustrates a semicircle graphical display of a physiological parameter in which a ghost value is shown simultaneously with a current value.

FIG. 19 illustrates a semicircle 1910 of a graphical display 1900 of a current value 1915 of a physiological parameter in which a ghost value 1920 is shown simultaneously with the current value 1915 to provide the clinician with historical context and a view of both current and past views at the same time. The semicircle graphical display 1900 may include one or more alarms or thresholds, such as those illustrated by 1930, 1940, 1945, and 1950. The ghost value 1920 may be shown in dashed lines, as a ghost/transparent way, a different size, a different color, a different position, a different font, or other distinguishing characteristic.

Figure 20:
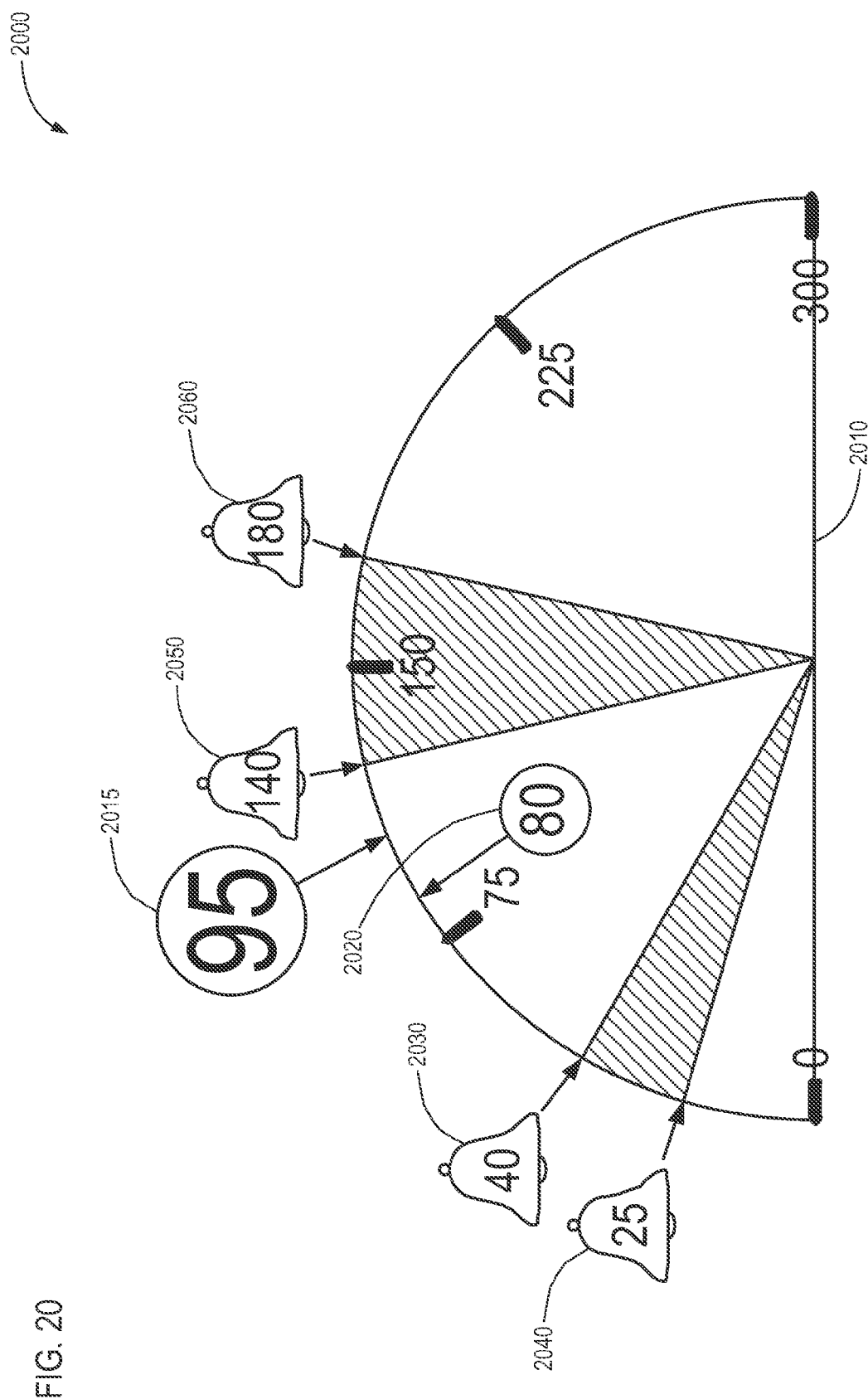
FIG. 20 illustrates an alternative semicircle graphical display of a physiological parameter in which a ghost value is shown simultaneously with the current value.

FIG. 20 illustrates an alternative semicircular gauge 2010 of a graphical display 2000 of a physiological parameter in which a historical value 2020 is shown simultaneously with the current value 2015. Various threshold values 2030, 2040, 2050, and 2060 may be shown on the graphical display and may be moved, deleted, renamed, and/or otherwise manipulated by a user (e.g., a clinician or other interested user).

Figure 21:
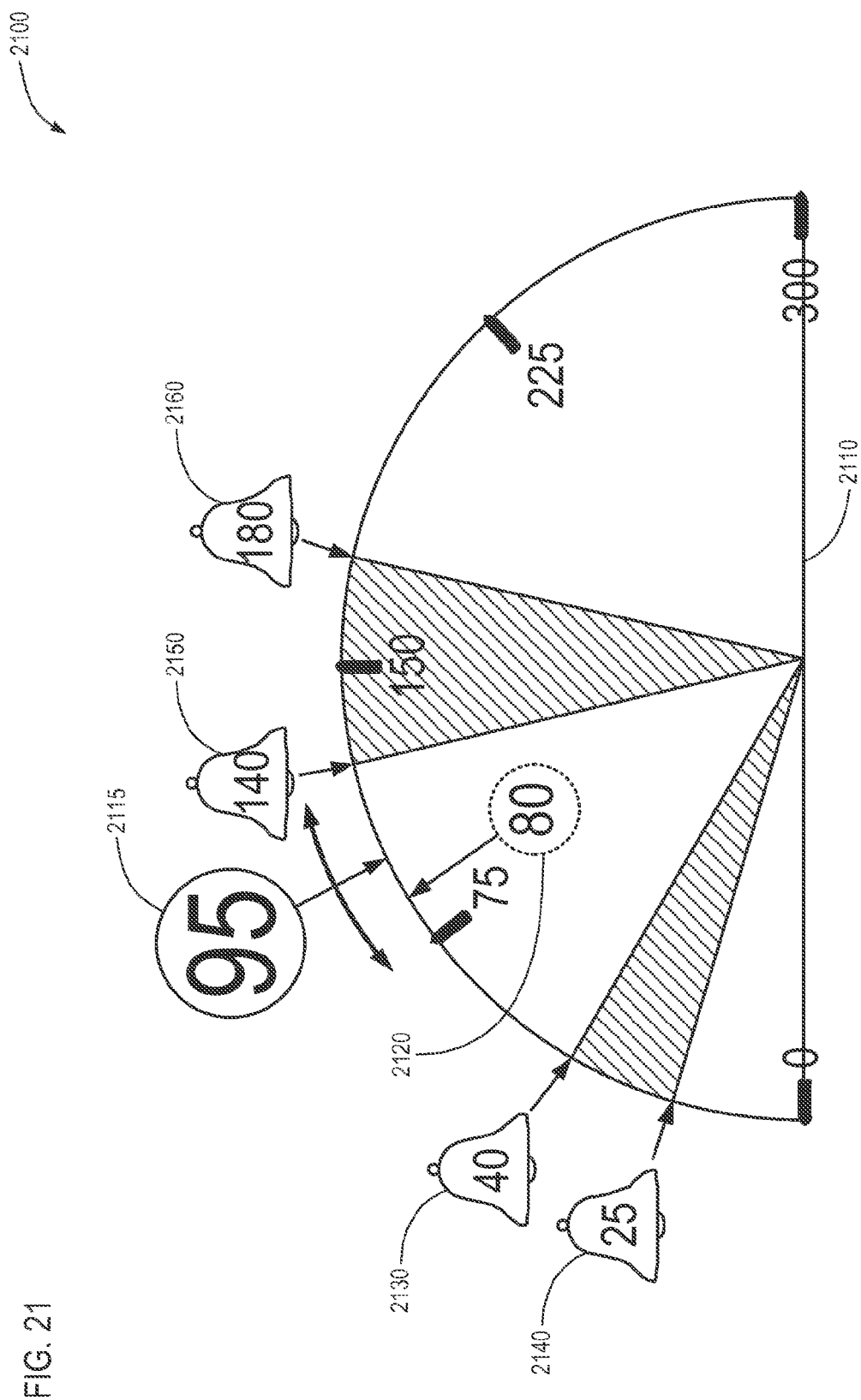
FIG. 21 illustrates a semicircle graphical display of a physiological parameter in which a range of recent variations in a current value of the physiological parameter are shown with an arrow.

FIG. 21 illustrates a semicircular gauge 2110 of a graphical display 2100 of a physiological parameter in which a range of recent variations from a current value 2115 are shown with an arrow. The arrow may extend to the right to a point corresponding to a maximum value of the physiological parameter within a recent time period. The arrow may extend to the left to a point corresponding to a minimum value of the physiological parameter within the same recent time period. The time period may be a few seconds, minutes, hours, or other period. In some embodiments, a ghost numerical value 2120 may be shown that represents an average value of the physiological parameter within the time period. As in other embodiments, alarms 2130, 2140, 2150, and 2160 represent various threshold values and may define one or more threshold, warning, or danger zones.

Figure 22:
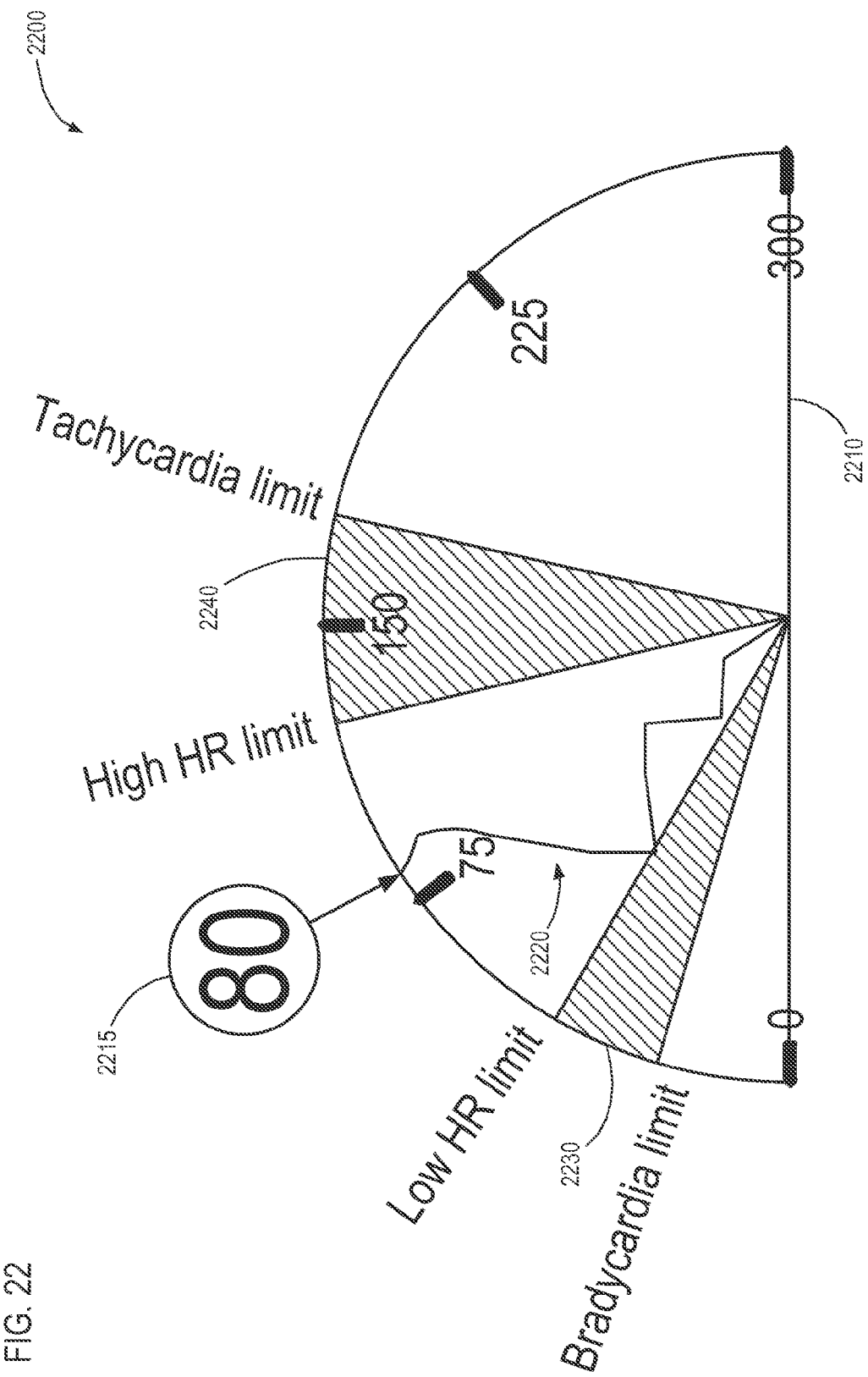
FIG. 22 illustrates a semicircle graphical display of a current physiological parameter with a line representation of historical physiological parameter values between the center and outer edges of the semicircle.

FIG. 22 illustrates a semicircular gauge 2210 of a graphical display 2200 showing various threshold zones 2230 and 2240. A current value 2215 of a physiological parameter is shown at a location along the outer perimeter of the semicircle 2210. A historical line 2220 shows historical values of the physiological parameter with the most recent values toward the perimeter of the semicircle and the oldest values of the physiological parameter toward the base of the semicircle. In some embodiments, time delineation marks may provide an indication of how long ago each historical value was sampled along the historical line 2220.

The historical line may represent a few minutes of historical values, a few seconds of historical values, or even hours, days, or weeks of historical values. In some embodiments, a user may select a point on the historical line via a touchscreen, stylus, mouse, or other device and a numerical value may be displayed. In some embodiments, numerical values for recent minimum values and recent maximum values may be displayed. In some embodiments, the historical line may be color coded based on being within one or more threshold zones 2230 and 2240. For example, a portion of historical line 2220 passing through zone 2230 may be color coded to indicate that it was below a threshold value.

The systems and methods described herein may include any combination of embodiments taught herein. For example, the historical line 2220 of FIG. 22 may be combined with the ghost values, recent range arrows, and/or other historical value indicators.

Figure 23:
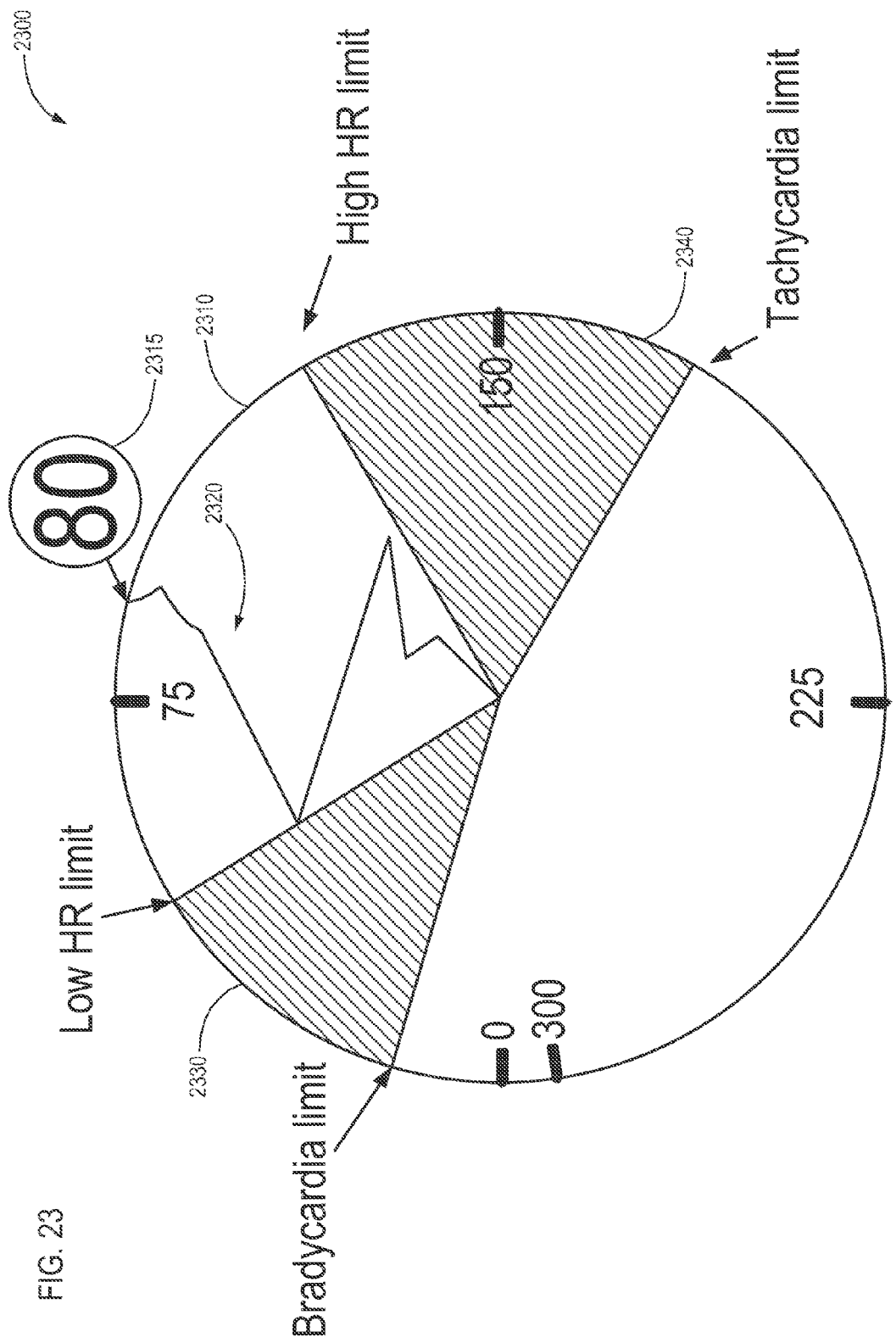
FIG. 23 illustrates a circular graphical display of a current physiological parameter similar to FIG. 22.

FIG. 23 illustrates a circular gauge 2310 of a graphical display 2300 showing a current value 2315 of a physiological parameter. The circular gauge 2310 may show an increased resolution as compared to the semicircular gauge of FIG. 22.

Figure 24:
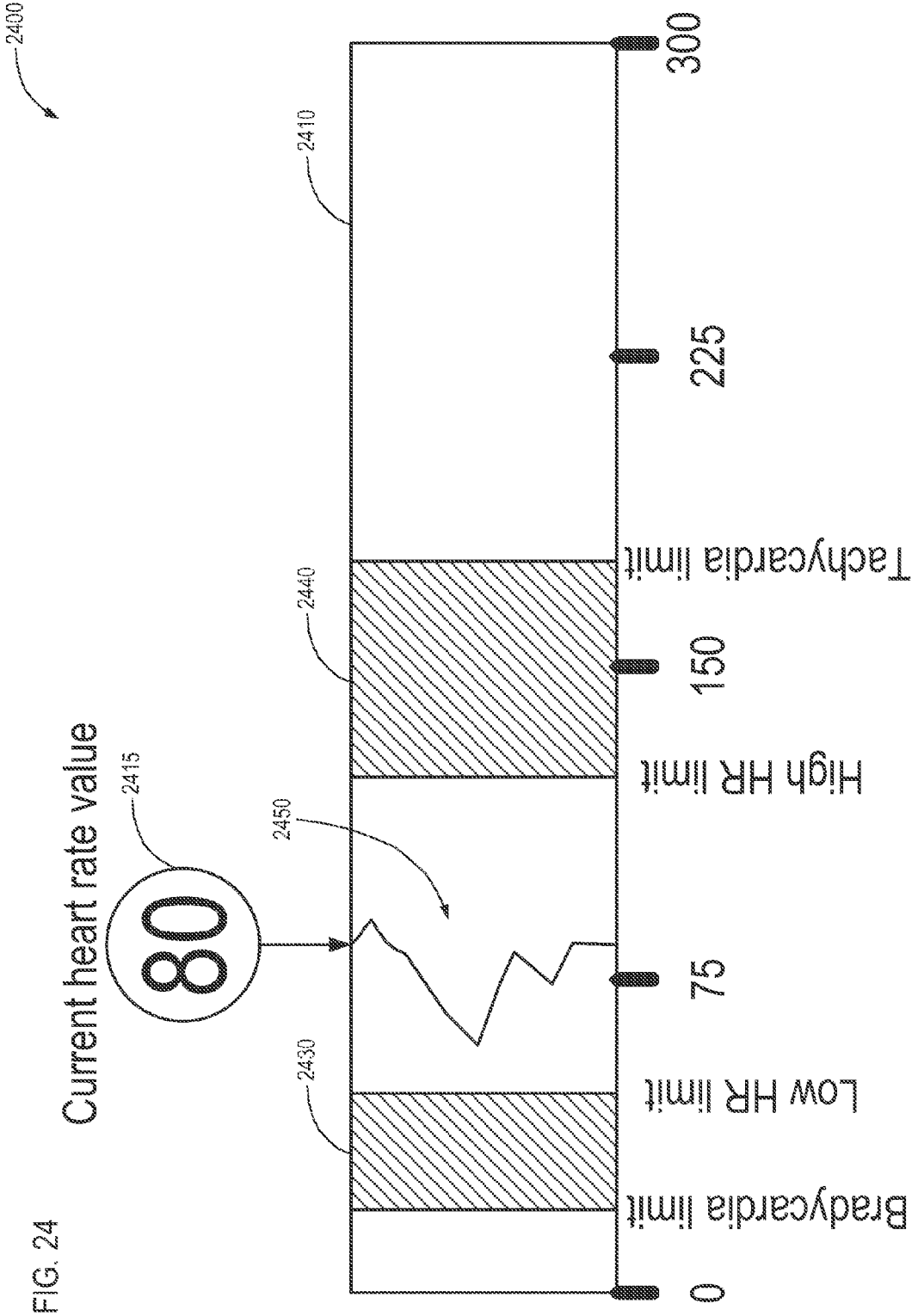
FIG. 24 illustrates a rectangular graphical display of a current physiological parameter similar to FIG. 22.

FIG. 24 illustrates a rectangular gauge 2410 of a graphical display 2400 that includes a current value 2415 of a physiological parameter along with a historical line 2450. The historical line 2450 shows historical values of the physiological parameter with the most recent values toward the top of the rectangular gauge and the older values toward the bottom of the rectangular gauge. In some embodiments, a user may adjust the time period represented by the distance between the top and bottom of the rectangular gauge and/or adjust the total height of the rectangular gauge. As in other embodiments, user-selectable alarms and threshold zones 2430 and 2440 may be shown in the graphical display 2400 as well.

This disclosure has been made with reference to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

This disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

What is claimed is:

1. A physiological parameter presentation system, comprising:
   a processor;
   an electronic input receiver configured to receive an electronic value corresponding to a measured physiological parameter of a patient;
   a data store configured to store a plurality of historical values of the measured physiological parameter;
   a display module in communication with the processor configured to generate a graphical display including a semicircular gauge along which are simultaneously positioned:
      a range of possible values for the physiological parameter including a minimum value and a maximum value;
      a visual representation of at least one threshold value between the minimum value and the maximum value;
      a numerical display of the current value of the measured physiological parameter;
      an indication of a range of variation of the measured value of the physiological parameter within a particular time period, wherein the indication of the range of variation extends in a first direction along the semicircular gauge from a point corresponding to the current value to a point corresponding to a maximum value of the measured physiological parameter during the particular time period, and wherein the indication of the range of variation extends in second direction opposite to the first direction along the semicircular gauge to a point corresponding to a minimum value of the measured physiological parameter within the particular time period; and
      a numerical historical comparator based on one or more of the historical values of the measured physiological parameter, wherein the numerical historical comparator is made visually distinguishable from the numerical display of the current value; and
   an electronic display output configured to output the generated graphical display to an electronic display.

2. The system of claim 1, wherein the numerical historical comparator comprises a historical value of the physiological parameter.

3. The system of claim 1, wherein the numerical historical comparator comprises a historical average of the physiological parameter during a prior time period.

4. The system of claim 1, wherein the numerical historical comparator is displayed as a ghost image proximate to the current value of the physiological parameter.

5. The system of claim 1, wherein the electronic input receiver comprises an input connector for connection to a sensor probe for measuring a physiological parameter of a patient.

6. The system of claim 1, wherein the electronic input receiver comprises a network communication port for receiving electronically transmitted data including the measured physiological parameter of a patient.

7. The system of claim 1, wherein the numerical display of the current value of the measured physiological parameter and the numerical historical comparator are positioned proximate a base of the semicircular gauge.

8. The system of claim 1, wherein the graphical display generated by the display module further comprises a first status icon configured to indicate a comparison of the current value of the measured physiological parameter with the at least one threshold value is acceptable, wherein the display module is configured to replace the first status icon with a second status icon when the comparison of the current value of the measured physiological parameter with the at least one threshold value is unacceptable.

9. The system of claim 1, further comprising a user-threshold receiver configured to receive one or more threshold value alarms.

10. The system of claim 1, wherein the indication of the range of variation comprises an arrow.

11. A non-transitory computer-readable storage medium storing instructions that, when executed by a processor, are configured to cause the processor to perform operations, the operations comprising:
receiving, via an electronic input receiver, an electronic value corresponding to a measured physiological parameter of a patient;
storing a plurality of historical values of the measured physiological parameter;
generating a graphical display including a semicircular gauge along which are simultaneously positioned a range of possible values for the physiological parameter including a minimum value and a maximum value, a visual representation of at least one threshold value between the minimum value and the maximum value, a numerical display of a current value of the measured physiological parameter, an indication of a range of variation of the measured value of the physiological parameter within a particular time period, and a numerical historical comparator based on one or more of the historical values of the measured physiological parameter, wherein the numerical historical comparator is made visually distinguishable from the numerical display of the current value, wherein the indication of the range of variation extends in a first direction along the semicircular gauge from a point corresponding to the current value to a point corresponding to a maximum value of the measured physiological parameter during the particular time period, and wherein the indication of the range of variation extends in second direction opposite to the first direction along the semicircular gauge to a point corresponding to a minimum value of the measured physiological parameter within the particular time period; and
outputting the generated graphical display to an electronic display.

12. The non-transitory computer-readable storage medium of claim 11, wherein the numerical historical comparator comprises a historical value of the physiological parameter.

13. The non-transitory computer-readable storage medium of claim 11, wherein the numerical historical comparator comprises a historical average of the physiological parameter during a prior time period.

14. The non-transitory computer-readable storage medium of claim 11, wherein the numerical historical comparator is displayed as a ghost image proximate to the current value of the physiological parameter.

15. The non-transitory computer-readable storage medium of claim 11, wherein the graphical display further comprises a first status icon configured to indicate a comparison of the current value of the measured physiological parameter with the at least one threshold value is acceptable, wherein the first status icon is replaced by a second status icon when the comparison of the current value of the measured physiological parameter with the at least one threshold value is unacceptable.

16. The non-transitory computer-readable storage medium of claim 11, wherein the operations further comprise:
receiving a second electronic value corresponding to a second measured physiological parameter of the patient;
generating a second graphical display that includes a range of possible values for the second physiological parameter including a minimum value and a maximum value, a visual representation of at least one threshold value between the minimum value and the maximum value, and a numerical display of the current value of the second measured physiological parameter; and
outputting the second generated graphical display to the electronic display for simultaneous display with at least one other graphical display associated with a different physiological parameter.

17. The non-transitory computer-readable storage medium of claim 11, wherein the indication of the range of variation comprises an arrow.

\* \* \* \* \*